US005707641A

United States Patent [19]

Gertner et al.

[11] Patent Number: 5,707,641
[45] Date of Patent: Jan. 13, 1998

[54] FORMULATIONS COMPRISING THERAPEUTICALLY-ACTIVE PROTEINS OR POLYPEPTIDES

[75] Inventors: Avi Gertner, Kfar Saba; Yosef Rubinstein, Ness Ziona, both of Israel

[73] Assignee: Pharmaderm Research & Development Ltd., Ness Ziona, Israel

[21] Appl. No.: 322,154

[22] Filed: Oct. 13, 1994

[51] Int. Cl.$^6$ .................................................. A61K 9/10
[52] U.S. Cl. .......................... 424/422; 424/484; 424/449
[58] Field of Search ...................................... 424/486, 422, 424/449, 434

[56] References Cited

U.S. PATENT DOCUMENTS

| | | | |
|---|---|---|---|
| 5,179,079 | 1/1993 | Hansen et al. | 514/970 |
| 5,324,521 | 6/1994 | Gertner et al. | 424/449 |
| 5,332,577 | 7/1994 | Gertner et al. | 424/449 |

FOREIGN PATENT DOCUMENTS

| | | |
|---|---|---|
| 85/05036 | 11/1985 | WIPO. |
| 92 18147 | 10/1992 | WIPO. |

OTHER PUBLICATIONS

Jacobs, M.A.J.M. et al., *Diabetes*, vol. 42: pp.1649–1655 (1993).
*Martindale*, 29th Ed., pp. 392–393.
*Martindale*, 29th Ed., p.1570.
Merck Index, 11th Ed., monographs 4887, 4889, 4890.
Novo Nordisk Pharmaceutical Products, pp. 1028–1037.
Willimann, H.L., et al., Lecithin organogels as matrix for the transdermal transport of drugs, Biochemical and Biophysical Research Communications, 1991, v. 177, No.3, pp. 897–900.
Nishihata, T., et al., Enhanced intestinal absorption of insulin in rats in the presence of Sodium 5-Methoxysalicylate, Diabetes, 1981, vol. 30, pp. 1065–1067.
Cookson, Clive, Gaining the upper hand, Financial Times, Sep. 17, 1993.
*Insulin*, pp. 1501–1502.
Sanders, L.M., Drug delivery systems and routes of administration, European Journal of Drug Metabolism and Pharmacokinetics 1990, pp. 95–102, vol. 15, No. 2.
Verhoef, J.C., et al., Transport of peptide and protein drugs across biological membranes, European Journal of Drug Metabolism and Pharmacokinetics, 1990, 83–93, vol. 15, No. 2.
Engel, R.H., Insulin: Intestinal Absorption as Water-in-Oil-in-Water Emulsions, Nature, 219, 1968, pp. 856–857.
Shichiri, M. et al., Enteral Absorption of Water-in-Oil-in-Water Emulsions in Rabbits, Diabetologia, 10, 1974, pp. 317–321.

(List continued on next page.)

*Primary Examiner*—Thurman K. Page
*Assistant Examiner*—M. Sikha
*Attorney, Agent, or Firm*—Nixon & Vanderhye P.C.

[57] ABSTRACT

A pharmaceutical formulation which is adapted particularly for transdermal administration, and which comprises an aqueous emulsion or dispersion including, in addition to the aqueous phase, at least ingredients (a) and (b) of ingredients (a), (b) and (c): (a) as active ingredient, at least one therapeutically active protein or polypeptide; (b) at least one pharmaceutically acceptable emulsifier; (c) an oil phase comprising or consisting essentially of at least one ester of an aliphatic hydroxy compound containing 1–12 carbon atoms and 1–4 alcoholic hydroxy groups with an aliphatic carboxylic acid containing 8–24 carbon atoms and 1–3 carboxylic acid groups; provided that the therapeutic activity of the active ingredient in the formulation is such that the presence or the therapeutic effect of the active ingredient is detectable in the bloodstream within less than two hours after commencing transdermal administration, and further provided that when the active ingredient comprises insulin, the insulin is subjected to a pretreatment under predetermined conditions, prior to incorporation in the formulation.

27 Claims, 31 Drawing Sheets

OTHER PUBLICATIONS

Shichiri, M., et al., Short-term Treatment of Alloxan-Diabetic Rats with Intrajejunal Administration of Water-in-Oil-in-Water Insulin Emulsions, Diabetes, 24, 1975, pp. 971–976.

Liedtke, R.K., et al., Wirkung peroraler und transdermaler Insulin-Praparationen auf die Blutgukose-Konzentration bei Mäusen, Arzneim.-Forsch./Drug Res., 40, 1990, pp. 880–883.

Liedtke, R.K., et al., Transdermale Applikation von Insulin bei Typ-II-Diabetikern, Arzneim.-Forsch./Drug Res., 40, 1990, pp. 884–886.

Tachibana, K., et al., Transdermal delivery of insulin by ultrasonic vibration, J. Pharm. Pharmacol., 43, 1991, pp. 270–271.

Jacobs, M.A.J.M., et al., The Pharmacodynamics and Activity of Intranasally Administered Insulin in Healthy Male Volunteers, Diabetes, 42, 1990, pp. 1649–1655.

FORMULATIONS COMPRISING THERAPEUTICALLY-ACTIVE PROTEINS OR POLYPEPTIDES

FIELD AND BACKGROUND OF THE INVENTION

The present invention relates to pharmaceutical formulations, which are useful for transdermal or parenteral administration of therapeutically-active proteins and polypeptides.

Delivery systems and routes of administration for peptide and protein drugs have been reviewed, e.g., in Sanders, L. M., Eur. J. Drug Metab. Pharmacokinet., 15(2): 95–102 (1990). This article notes that, with regard to possible transdermal administration, the stratum corneum presents an effective barrier in particular, to relatively large peptides and proteins; and that iontophoretic delivery uses fluxes of current which certainly damages the skin.

Verhoef, J. C. et al, in Eur. J. Drug Metab. Pharmacokinet., 15(2): 83–93 (1990), review the transport of peptide and protein drugs through the intestinal, buccal, nasal and pulmonary absorptive membranes, as well as transdermal penetration. Regarding transdermal administration, this article notes the disadvantages of poor percutaneous transport and appreciable intracutaneous breakdown.

Diabetes mellitus due to inadequate insulin secretion, or lack of insulin, is extremely widespread. Treatment of this disease by injection or infusion of insulin is predominantly via the subcutaneous route and to a minor extent via the intravenous or intramuscular route. These methods of administration have the disadvantage that once given, they cannot be withdrawn, e.g. in the case of development of hypoglycemia or other adverse patient reactions. In this connection, it is noted that up to 7% of deaths in insulin-dependent diabetics have been attributed to hypoglycemia.

Thus, there would be a great advantage in administering insulin (and for that matter other proteins and polypeptides) transdermally, in that a transdermal patch can be readily withdrawn in case of adverse reactions developing in the patient. Moreover, transdermal administration is a more convenient and user-friendly mode of drug administration than, e.g., the daily injection regimen which is widely used clinically at the present day in the case of insulin. However, research into administration of insulin, for example, by the transdermal route, or by routes other than injection or infusion, have not resulted in any practical clinical use, up to the present time.

Engel, R. H. et al, in Nature 219: 856–57 (1968), have described experiments in which anesthetized rats or gerbils were injected intraduodenally with emulsified insulin, at a rate of 50–150 iu insulin/kg body weight, resulting in a 57% reduction in the glucose level after one hour, from a 100 units/kg injection, whereas use of aqueous insulin under these conditions gave a result which did not differ significantly from a control experiment. Intravenous administration of emulsified insulin, at a rate of 100 iu insulin/kg body weight, to alloxanized rats, gave a 21±3% decrease in the blood glucose level (aqueous insulin: 16±2%). The emulsified insulin was in the form of water-in-oil-in-water (W-O-W) emulsions, prepared by sonication of an oil phase of 0.03M palmitic acid in trioctanoin, with an aqueous insulin phase containing 0.003M $ZnCl_2$, the resulting oil-in-water emulsion (apparently containing zinc palmitate, said to act as a partial stabilizer) then being mixed similarly with a second aqueous phase containing 1% sodium lauryl sulfate, the product W-O-W emulsion being adjusted to pH 6.5.

In Shichiri, M. et al, Diabetologia 10: 317–21 (1974) and Shichiri, M. et al, Diabetes 24: 971 (1975), there is described administration of W-O-W insulin emulsions to the jejunum in rabbits, or in alloxan-diabetic rats, which at respective dosage rates of 10–150 or 250–500 iu insulin/kg body weight are said to produce a significant and consistent increase in plasma insulin, followed by a fall in blood glucose. The ingredients of the emulsions closely followed Engel et al, loc cit, except that trioctanoin was replaced by "octyl-decyl triglyceride". The emulsions were also administered orally with an apparent 50% success rate as determined by responses in rabbits.

Liedtke, R. K. et al, in Arzneim.-Forsch./Drug Res. 40(II) (8): 880–3 (1990), describe oral and transdermal administration of lipid formulations of insulin to mice. The formulations appear to be the same as or similar to those of Shichiri, M. et al, loc cit. Glucose level lowering effects after transdermal administration were weaker than after opal application. In the first of two transdermal tests, no glucose reduction was recorded until 4 hours had elapsed, and (compared with placebo) the reduction in glucose at 8 hours was no more from that at 6 hours. In the second transdermal test, compared with placebo, there was a 14% reduction in glucose at 2 hours after commencement, which rose to 44% at 4 hours but dropped to 30% at 8 hours.

Liedtke, R. K. et al, in Arzneim.-Forsch./Drug Res. 40(II) (8): 884–6 (1990), describe supplementation with transdermal insulin (apparently administered in a similar manner to Liedtke, R. K. et al, loc cit), of oral medication with sulfonylurea.

Tachibana, K. et al, in J. Pharm. Pharmacol., 43 (4): 270–1 (1991), describe the technique of ultrasonic vibration to deliver insulin through the skin of hairless mice, immersed in a bath of neutral aqueous insulin.

The skilled reader will appreciate that the pertinent literature shows that transdermal transport of polypeptides or proteins in general, and insulin in particular, is difficult to achieve, and that whereas oral administration of insulin has not been achieved satisfactorily to the present day, attempted transdermal administration of insulin making use of aqueous emulsions of lipid-type substances is even less effective than oral administration. The literature is thus hardly encouraging of the possibility that the use of such emulsions might provide a means of administering polypeptides or proteins (e.g. insulin) by the transdermal route.

In U.S. Ser. No. 07/876,153 as originally filed Apr. 30, 1992, in the name of the present inventors, there was described and claimed a pharmaceutical composition for use in the transdermal administration of a medicament intended to be detectable in the blood stream within two hours after administration, comprising the medicament and a pharmaceutically acceptable carrier therefor consisting essentially of at least one compound selected from the group consisting of esters of $C_{8-24}$ fatty acids with at least one aliphatic $C_{2-12}$ hydroxy compound containing 2-3 hydroxy groups, excepting monoglycerides.

In U.S. Ser. No. 07/929,485 (a continuation of U.S. Ser. No. 653,393 filed Feb. 11, 1991, and now abandoned), in the name of the present inventors, now U.S. Pat. No. 5,324,521, there is described and claimed a non-adhesive matrix for use as a dosage form in the transdermal administration of a medicament to a mammal which comprises a porous, non-adhesive absorbent perforate solid support having absorbed thereon a mixture comprising the medicament and the pharmaceutically acceptable carrier as defined in the preceding paragraph.

Neither U.S. Ser. No. 07/876,153 nor U.S. Ser. No. 07/929,485 are concerned with or suggest the use of aqueous emulsions as transdermal carriers for medicaments. The entire contents of U.S. Ser. No. 07/876,153 and U.S. Ser. No. 07/929,485 are explicitly incorporated by reference herein.

Jacobs, M. A. J. M., et al, in Diabetes, 42: 1649-55 (1993), report the results of a study using intranasal insulin in presence of didecanoyl-α-phosphatidyl choline as absorption enhancer; in all cases examined, the bioavailability of intranasally administered insulin was <15% of the bioavailability of insulin administered subcutaneously or intravenously.

SUMMARY OF THE INVENTION

The present invention provides in one aspect a pharmaceutical formulation, useful particularly for transdermal or parenteral administration to mammals, which formulation comprises an aqueous emulsion or dispersion including, in addition to the aqueous phase: as active ingredient, at least one therapeutically active protein or polypeptide; at least one pharmaceutically acceptable emulsifier; and, preferably, an oil phase comprising or consisting essentially of at least one ester of an aliphatic hydroxy compound containing 1-12 carbon atoms and 1-4 alcoholic hydroxy groups with an aliphatic carboxylic acid containing 8-24 carbon atoms and 1-3 carboxylic acid groups; provided that the therapeutic activity of the active ingredient in the formulation is such that the presence or the therapeutic effect of the active ingredient is detectable in the bloodstream within less than two hours, preferably within less than 1.5 hours and more preferably within less than one hour, after commencing transdermal administration, and further provided that when the active ingredient comprises insulin, this is subjected to a pretreatment under predetermined conditions. The present inventors have surprisingly discovered that when attempts are made to administer insulin transdermally in absence of such a pretreatment (but otherwise applying the formulation of the invention) the best results are not obtained, whereas inclusion of such pretreatment dramatically and unexpectedly increases the effect of insulin in reducing glucose levels in the bloodstream. The invention accordingly also provides a pharmaceutical formulation which is adapted particularly for transdermal administration, and which comprises at least one carrier, diluent or adjuvant, together with insulin as active ingredient, provided that the insulin has been subjected to a pretreatment under predetermined conditions, with the result that its therapeutic activity is such that its presence or its therapeutic effect is detectable in the bloodstream within less than two hours after commencing transdermal administration.

The beneficial effect of pretreating insulin in accordance with the invention is all the more surprising in view of the manufacturer's recommendation that if refrigeration of the commercial preparation is not maintained, it should be thrown out after keeping for one month at room temperature, with the implication that it will then have become ineffective, or at least unreliable. Once a person skilled in the art has been taught the desirability of the pretreating step in accordance with the present invention, he would have no difficulty in ascertaining effective conditions of pretreatment. By way of illustrative exemplification only, it is presently believed that pretreatment should be carried out at above refrigeration temperatures and preferably at ambient temperature, or up to e.g. blood temperature, i.e. about 37° C., for a period of several days or weeks, or e.g. up to about one month.

While, as stated above, the present invention includes pretreated pharmaceutical formulations containing insulin without emulsifier or oil phase, nevertheless use of emulsifier and/or oil phase appears to be advantageous in that in their absence the formulations intended for transdermal administration might cause some skin irritation, which appears to be ameliorated (or prevented) by the presence of emulsifier and/or oil phase in the formulations. The pharmaceutical formulations of the invention intended for transdermal administration can also of course include a skin-irritation mitigation agent, if deemed desirable or necessary.

Also, as is shown in the illustrative Examples, the formulations in which emulsifier and/or oil phase is present may contain e.g. approximately 40% less insulin than the formulations in emulsifier and oil phase are absent, but nevertheless achieve similar or better activity, in relation to reduction of blood glucose levels, than when emulsifier and oil phase are absent.

In a particular embodiment, the therapeutic activity of the formulation, when the active ingredient comprises insulin, is such that in a bioassay based on subcutaneous injection of no more than 0.2 iu insulin/kg in healthy rabbits, including a control bioassay, the formulation is capable of exhibiting a peak of reduction of the blood glucose concentration, compared with the control, within no more than one hour from the time of injection.

In another aspect, the invention provides a matrix for transdermal administration of the above-defined active ingredient, which comprises a porous, absorbent, perforate and flexible monolaminar or polylaminar solid support, having absorbed thereon a pharmaceutical formulation as defined above. The matrix may comprise additionally a flexible breathable backing layer adhered to one side of the solid support, the backing layer having less absorbability for the pharmaceutical composition, than the flexible solid support.

The active ingredient is preferably insulin, in which case the pharmaceutical formulation of the invention may be used in a method for treating diabetes mellitus, by administration of the formulation which contains an effective diabetes mellitus treating amount of insulin. Although the formulation is by definition suitable for parenteral or transdermal administration, it is believed that it may have potential for treatment by intranasal, oral, buccal or rectal administration also, as well as for aerosol delivery by oral inhalation.

In yet another aspect, the invention provides a method for controlling glucose concentration in the blood of a diabetic patient, which comprises administering to the patient a pharmaceutical formulation according to the invention, when the active ingredient is insulin. In a particular embodiment, the pharmaceutical formulation is administered to the patient transdermally, e.g., by applying to the skin of the patient a matrix which comprises a porous, absorbent, perforate and flexible monolaminar or polylaminar solid support, having absorbed thereon the pharmaceutical formulation of the invention. As is noted elsewhere herein, the embodiment of the method of the invention wherein insulin is administered to a patient transdermally, has the particular advantage of being able to be withdrawn at will (e.g. if a hypoglycemic event occurs) and thus provides for avoiding or moderating hypoglycemia (or alternate hypoglycemic and hyperglycemic events), hypoglycemia being the unfortunate but virtually inevitable result of administering insulin by the conventional routes.

BRIEF DESCRIPTION OF THE DRAWINGS

The Figures of the Drawings, unless otherwise stated, depict the results of studies on formulations containing pretreated insulin according to embodiments of the invention, which are administered to a healthy human transdermally.

DETAILED DESCRIPTION OF THE INVENTION

Figure 1A:
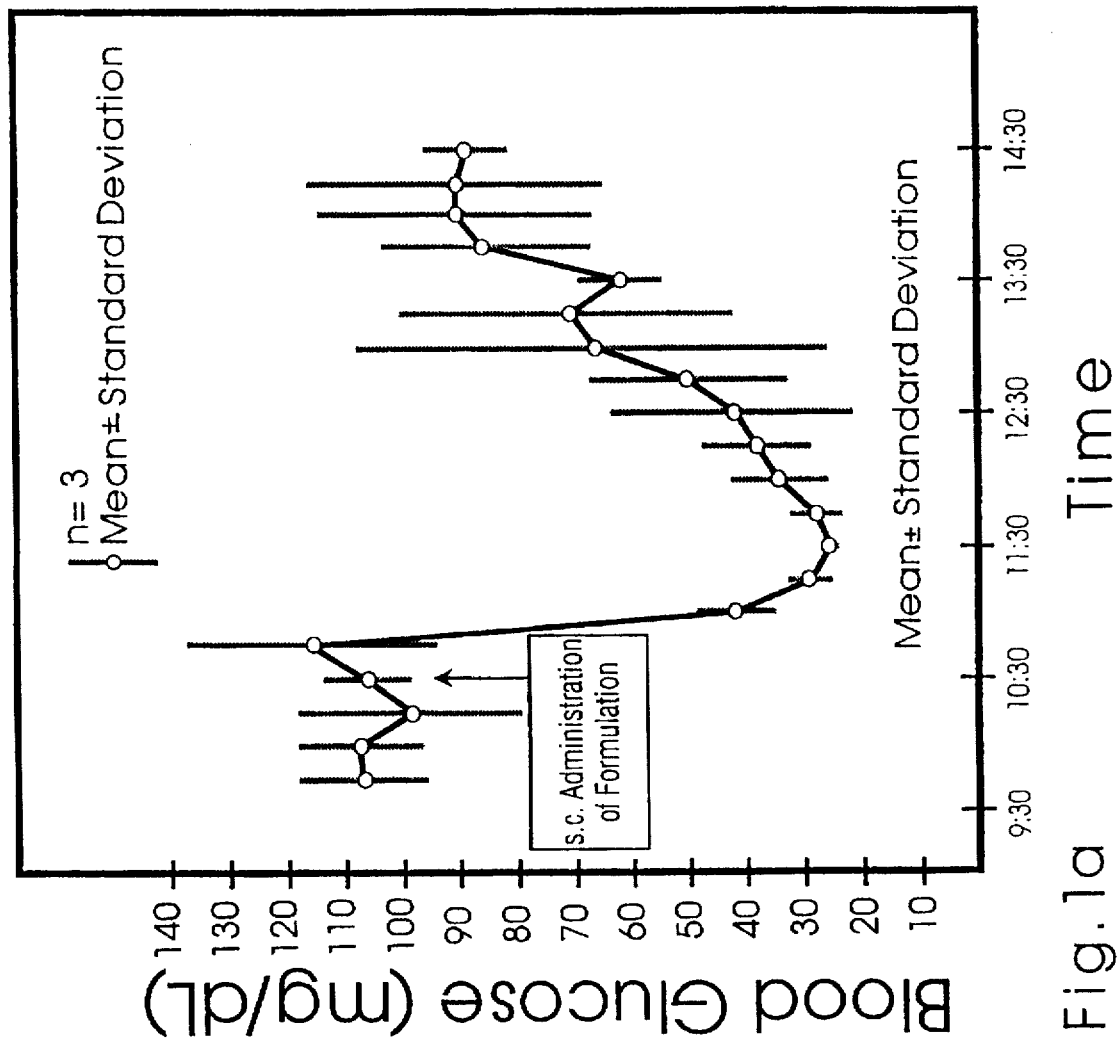
FIGS. 1a-1g depict graphically the results of a bioassay in which formulations according to embodiments of the invention are administered to healthy rabbits subcutaneously.

When oil phase is present in accordance with an embodiment of the invention, this may comprise at least one ester as defined above. It is contemplated for example that in this embodiment there may be present some other substance in minor amount, e.g. paraffins, as well as for example, preservatives, stabilizers and/or antioxidants, which in any event do not prevent the formulation from functioning therapeutically as described herein.

In a presently preferred embodiment of the oil phase of the formulation, however, this consists essentially of at least one ester as defined above. Such definition effectively excludes extraneous ingredients, such as free palmitic acid, which appears to be an essential ingredient in a number of similar emulsions which have been described in some of the above-referenced literature articles.

As persons of the art will be aware, the esters which may be utilized in the present formulations may be regarded as being constituted from hydroxy-containing components and carboxylic acid components. The hydroxy-containing components of such esters in the present instance are aliphatic hydroxy compounds containing 1-12 carbon atoms, preferably 1, 2, 3, 4, 5 or 6 carbon atoms, and 1, 2, 3 or 4 alcoholic hydroxy groups in the molecule. Thus, e.g., the alcohols may be monohydric alcohols such as methyl, ethyl, propyl, isopropyl, butyl, hexyl, octyl, decyl or dodecyl alcohols, or polyhydric alcohols such as ethylene glycol, polypropyleneglycol, glycerol or pentaerythritol.

The carboxylic acid components of the esters which are utilized in the present invention are aliphatic carboxylic acids containing 8-24 carbon atoms and 1-3 carboxylic acid groups. Presently preferred are such acids, more preferably which are monocarboxylic acids, selected from saturated carboxylic acids and carboxylic acids containing ethylenic unsaturation.

In a particular embodiment, the oil phase comprises or consists essentially of at least one ester selected from monoglycerides, diglycerides and triglycerides of the defined class of carboxylic acids, more particularly of saturated monocarboxylic acids and/or monocarboxylic acids containing ethylenic unsaturation.

Without prejudice to the fact that suitable aliphatic acid components if the esters may contain any number of carbon atoms from 8 to 24 inclusive, and 1, 2 or 3 carbon atoms, such acids may be selected from, for example, caprylic, captic, lauric, palmitic, stearic, arachidic, behenic, lignoceric, oleic, elaidic, petroselinic, linoleic, alpha-linolenic (9,12,15-octadecatrienoic acid), gamma-linolenic, linolelaidic, arachidic, 11-eicosenoic, 11,14-eicosadienoic, 11,14,17-eicosatrienoic, 8,11,14,-eicosatrienoic, arachidonic, 5,8,11,14,17-eicosapentaenoic, erucic and nervonic acids.

The ester component of the oil phase of the formulations of the invention may be a single ester or a mixture of different esters. Natural oils and fats are mixtures of triglyceride esters and are in general suitable for use in the present formulations. Non-limiting examples of such natural mixtures of esters are almond, coconut, corn, cottonseed, grapeseed, linseed, olive, palm-kernel, palm, peanut, rapeseed, safflower, sesame, soybean, sunflower-seed and walnut oils. Mixtures of these natural oils may be used, as well as fractions of such oils. An example of a useful such fraction is a commercially available liquid coconut oil fraction, of which the carboxylic content (as triglyceride) is: caprylic acid 54.2%, captic acid 45.1% and lauric acid 0.80%.

The oils mentioned in the preceding paragraph are of course by no means exhaustive of the natural oils which may be used in the present formulations. In a particular embodiment, the oil is one which contains gamma-linolenic acid (as the triglyceride ester), such as evening primrose oil, borage oil or fungal lipid. It appears that these oils may improve a diabetic patient's neuropathic condition, insofar as neuropathy is a side-effect of diabetes.

When the active ingredient is insulin, it is intended that any kind of insulin used in clinical practice at the present time, whether, for example, genetically engineered human insulin, or insulin of animal origin, e.g. of bovine or porcine origin, may be used in the present invention.

Insulin for clinical use as produced commercially contains small amounts of zinc, so that this may also be present in the formulations of the invention containing insulin. In the case that zinc-free insulin may be used clinically in the future, then correspondingly its use in the present invention is also contemplated.

The formulation of the invention is suitable for transdermal or parenteral administration, and possibly also for other forms of administration such as those mentioned above. In the case of insulin as the active ingredient in particular, the suitability for parenteral administration is based at least in part on the results reported herein of bioassays using subcutaneous administration to healthy rabbits, which showed in many cases that the present formulations were more effective in reducing blood glucose concentrations than a commercially produced formulation, while the potential for oral administration is based at least in part on the literature reviewed above which tends to show that (so far as was then known) activity on oral administration of the same formulation was of greater efficacy that on transdermal administration.

As noted above, one of the alternative criteria of the preferred pharmaceutical formulation of the invention, where the active ingredient comprises insulin, is that its therapeutic activity is such that in a bioassay based on subcutaneous injection of no more than 0.2 iu/kg in healthy rabbits, including a control bioassay, the formulation is capable of exhibiting a peak of reduction of the blood glucose concentration, compared with the control, within no more than one hour from the time of injection. It is particularly preferred that this peak of reduction is at least 50% below the control value of blood glucose concentration at the same elapsed time from the time of injection.

Figure 6:
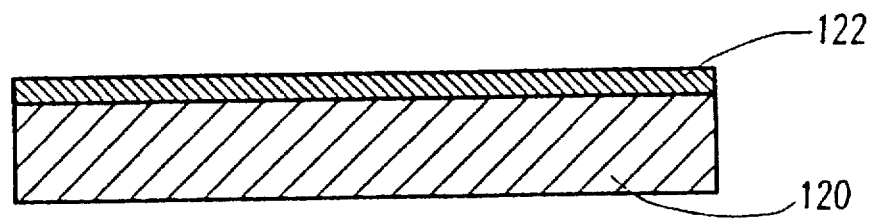
FIGS. 6 and 7 show side views of different embodiments of matrices according to the invention.
Figure 7:
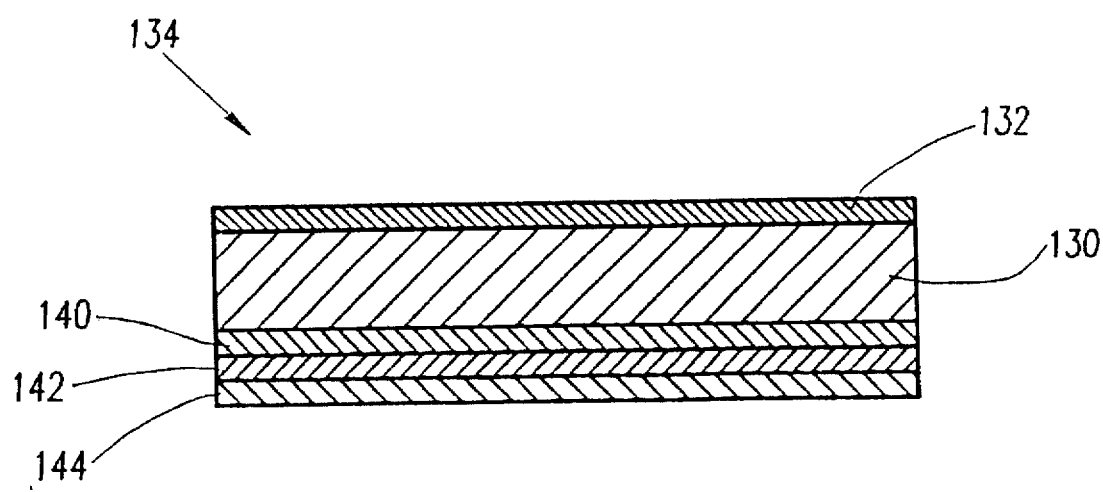

While the formulations in accordance with the invention may be administered parenterally or transdermally in any dosage form for this purpose known in the art, the matrix according to the invention may of course be used for transdermal administration, in a non-limiting embodiment. Thus, for example, FIG. 6 shows a side view of a particular embodiment of a matrix according to the present invention, comprising a porous flexible support layer 120, having a flexible breathable backing layer 122 adhered thereto. FIG. 7 shows a side view of another embodiment of the device of the invention, comprising a porous flexible support layer 130, having a flexible breathable backing layer 132 adhered thereto, which is included in a multilayer system shown generally by the reference numeral 134, which multilayer system consists of at least two layers, i.e. layer 130 and at least one other layer 140. The multilayer system can of course otherwise consist of three or more layers including e.g. layers 142 and 144. FIG. 7 is purely illustrative and does not limit the number of layers in the system or their order. The different layers in the system may have the same, similar or different absorbabilities for the pharmaceutical composition, and will be designed to dispense such composition at the layer nearest the skin so as to transdermally administer the formulation therethrough.

The emulsifier used in a particular embodiment of the present formulation may be any pharmaceutically acceptable emulsifier which gives rise to an emulsion (or facilitates the formation of a dispersion), from which, e.g., in the case of transdermal administration, an effective amount for the intended purpose of therapeutically active protein or polypeptide may be transferred into the blood stream of a patient. Without prejudice to this generalization, it has been found that lecithin and polyoxyethylene sorbitan monocarboxylate esters e.g. Tween 80 (polyoxyethylene (20) sorbitan monooleate) are been effective emulsifiers. Without being limited by any theory of operation, it may be that these emulsifiers are effective, especially because they contain inter alia esterified carboxylic groups, similarly to the oil phase (esters) of the emulsion formulation, in a preferred embodiment of the invention.

In a particular embodiment, when the oil phase is absent from the pharmaceutical formulations of the invention, then the formulations may exclude didecanoyl-α-phosphatidyl choline.

DESCRIPTION OF EXEMPLIFIED EMBODIMENTS

Preparation of Formulations containing Insulin
Materials

The aqueous insulin solution known as Actrapid (Registered Trade Mark) HM is produced by Novo Nordisk A/S (Bagsvaerd, Denmark). It is a neutral insulin injection containing genetically engineered human monocomponent insulin, 100 iu (3.5 mg) in 1 ml, which contains additionally 3 mg m-cresol as preservative as well as 1.4–1.8% (w/v) glycerol. Note: for the purpose of Examples 1–8, below, the Actrapid HM was pretreated by keeping at ambient temperature for one month, prior to making the specified formulations.

Lecithin was 100% pure soya-lecithin granules produced by Lucas Meyer (Hamburg, Germany), and contained 5 mg Na/100 g. The granules were ground to a powder prior to use.

FORMULATION A

A mixture of Actrapid HM (6 ml) and lecithin powder (1 g) was stirred rapidly at 35° C. for 90 minutes, 4 ml fractionated liquid coconut oil (Estasan GT 8-60 3580 from Unichem Ltd.) was added, and the whole was again stirred rapidly at 35° C. for 90 minutes.

FORMULATION AA

The procedure of Formulation A was followed with an additional final step of sonication for two minutes with a LECO sonifier (Model UC 200).

FORMULATION B

A mixture of Actrapid HM (6 ml) and lecithin powder (1 g) was stirred rapidly at 35° C. for 90 minutes, 4 ml refined soybean oil (Izhar, Israel) was added, and the whole was again stirred rapidly at 35° C. for 90 minutes.

FORMULATION C

A mixture of Actrapid HM (6 ml) and lecithin powder (1 g) was stirred rapidly at 35° C. for 90 minutes, 4 ml unrefined coconut oil (Health & Life, Ltd., Baidon, England) was added, and the whole was again stirred rapidly at 35° C. for 90 minutes.

FORMULATION D

A mixture of Actrapid HM (6 ml) and lecithin powder (1 g) was stirred rapidly at 35° C. for 90 minutes, 4 ml olive oil ("Extra Virgin", Hanat Yani, Israel) was added, and the whole was again stirred rapidly at 35° C. for 90 minutes.

FORMULATION E

A mixture of Actrapid HM (6 ml) and Tween 80 (2.5 ml technical grade) was stirred rapidly at 35° C. for 90 minutes, 4 ml fractionated liquid coconut oil (Estasan GT 8-60 3580 from Unichem Ltd.) was added, and the whole was again stirred rapidly at 35° C. for 90 minutes.

FORMULATION F

A mixture of 2 ml each of formulations D and E was rapidly stirred at 30° C. for 45 minutes.

FORMULATION G

A mixture of Actrapid HM (6 ml) and Tween 80 (3 ml technical grade) was stirred rapidly at 35° C. for 90 minutes, 4 ml olive oil ("Extra Virgin", Hanat Yani, Israel) was added, and the whole was again stirred rapidly at 35° C. for 90 minutes.

FORMULATION H

A mixture of Actrapid HM (6 ml) and Tween 80 (3 ml technical grade) was stirred rapidly at 35° C. for 90 minutes, 4 ml evening primrose oil (analytical grade, R. C. Treatt, U.K.) was added, and the whole was again stirred rapidly at 35° C. for 90 minutes.

Use of Formulations containing Insulin

In the following examples, blood glucose concentration was determined with the aid of "Glucostix" reagent strips (Miles Ltd., Ames Division, Bayer Diagnostics UK Ltd.) and Ames Olucometer (Registered Trade Mark) (Miles Inc., Diagnostics Division). In the experiments performed on rabbits, periphery capillary blood was taken from the tail. In the studies conducted on human subjects, blood was taken from the finger.

EXAMPLE 1

Method

A bioassay was used to determine the insulin activity of the formulation. Thus, its capacity to lower the blood glucose concentration, on subcutaneous administration, was tested in locally bred healthy rabbits, after overnight fasting, but with free access to water. Three approximately one-year old rabbits (2 female, 1 male) weighing 5 kg each, were used in this test. Prior to injection, blood glucose concentration was determined four times at 15 minute intervals. After subcutaneous injection of 0.012 ml of Formulation A, which contained 1 iu of insulin, at the rear mid-dorsal region of each rabbit using a "Microfine +" disposable insulin syringe (Beckton Dickinson Insulin Syringe Ltd., Pottery Road, Dun Laoghaire, Co. Dublin, Ireland), blood glucose concentration was determined at 15 minute intervals for the next four hours. For comparison purposes, an amount of Actrapid HM containing 1 iu insulin was injected and its effect monitored under the same conditions.

Formulations B, C, D and E were also tested under similar conditions.

Results

Figure 1B:
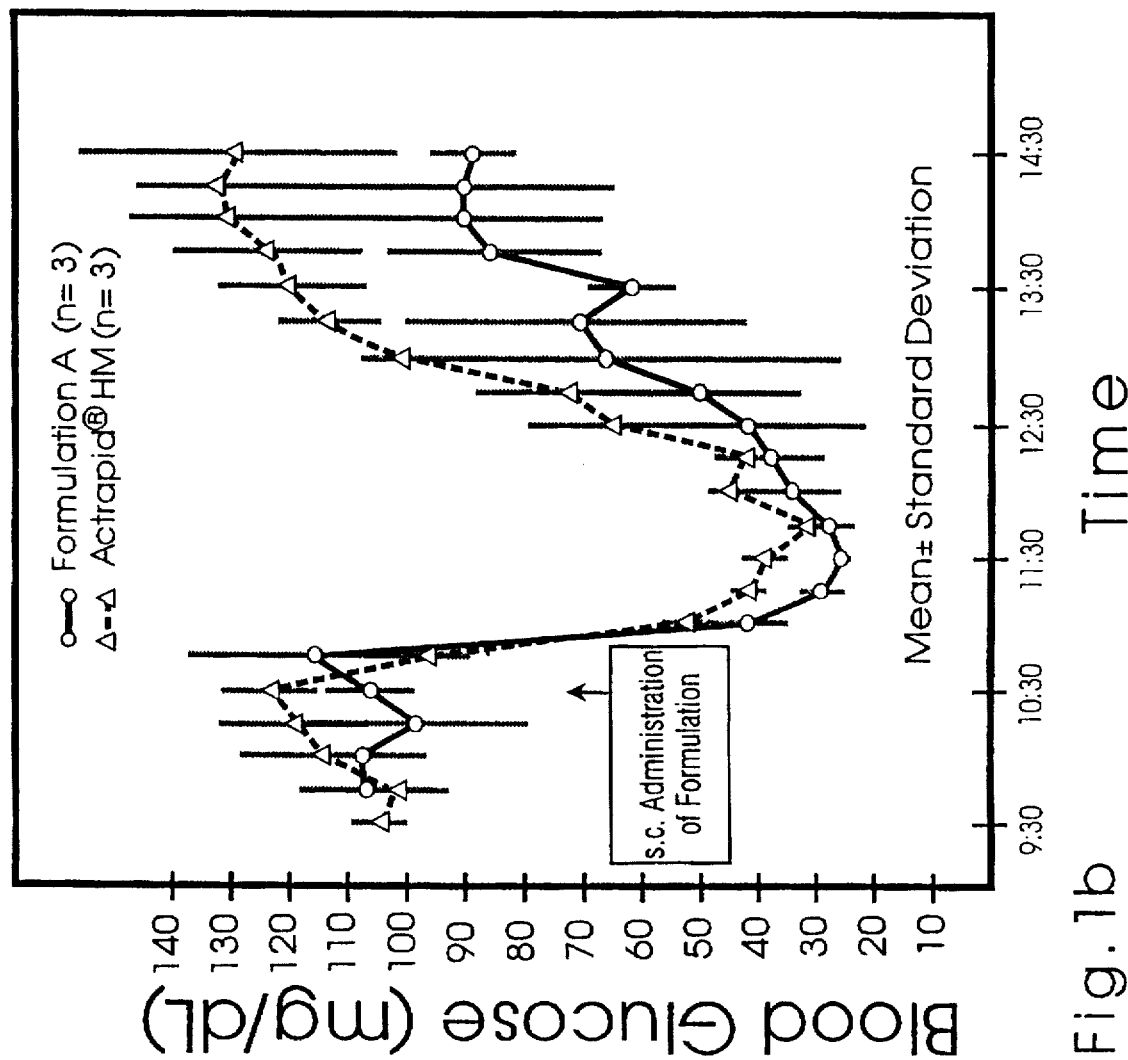

Using Formulation A, blood glucose concentration averaged 105 mg/dl prior to injection and reached the lowest concentration of 26 mg/dl on the sample taken at 60 minutes after injection, a reduction of approximately 75%. After 60 minutes, blood glucose concentration gradually increase to a figure of 90 mg/dl (average) at the end of the four-hour period, still 15% less than the pre-injection concentration (FIG. 1a). FIG. 1b compares the effectiveness of Actrapid HM containing the same quantity of insulin as the present formulation, injected subcutaneously, in lowering the blood glucose concentration in rabbits. FIGS. 1c, 1d, 1e and 1f compare the effectiveness of Formulations B, C, D and E, respectively, with Formulation A.

Conclusions (i) This study shows in FIGS. 1a and 1b that Formulation A, in accordance with the invention, when injected subcutaneously in healthy rabbits, has a good capacity for lowering the blood glucose concentration at least equal to, and over part of the time period was more effective than, that of the same quantity of insulin in the form of Actrapid HM.

Figure 1C:
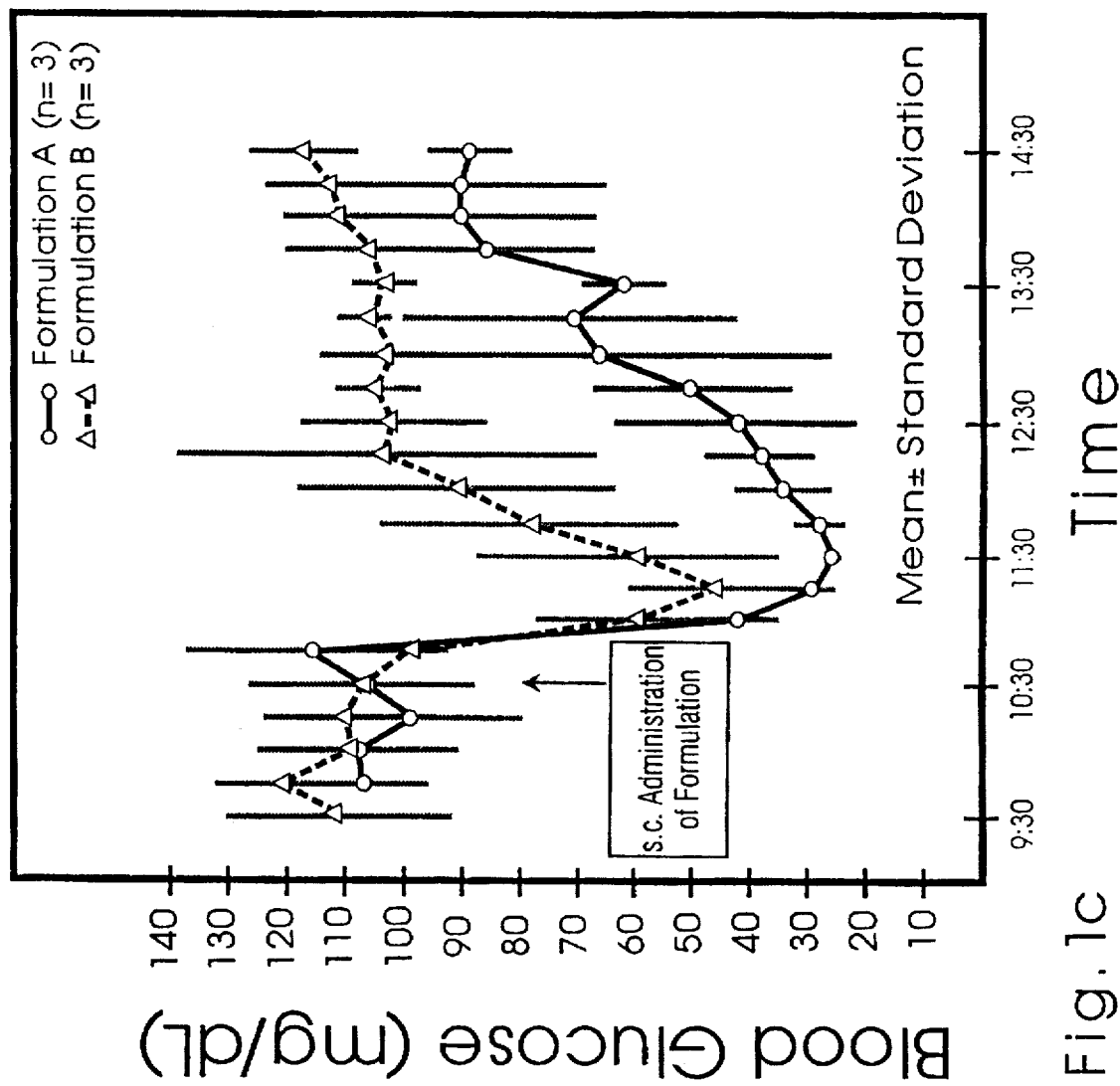
Figure 1D:
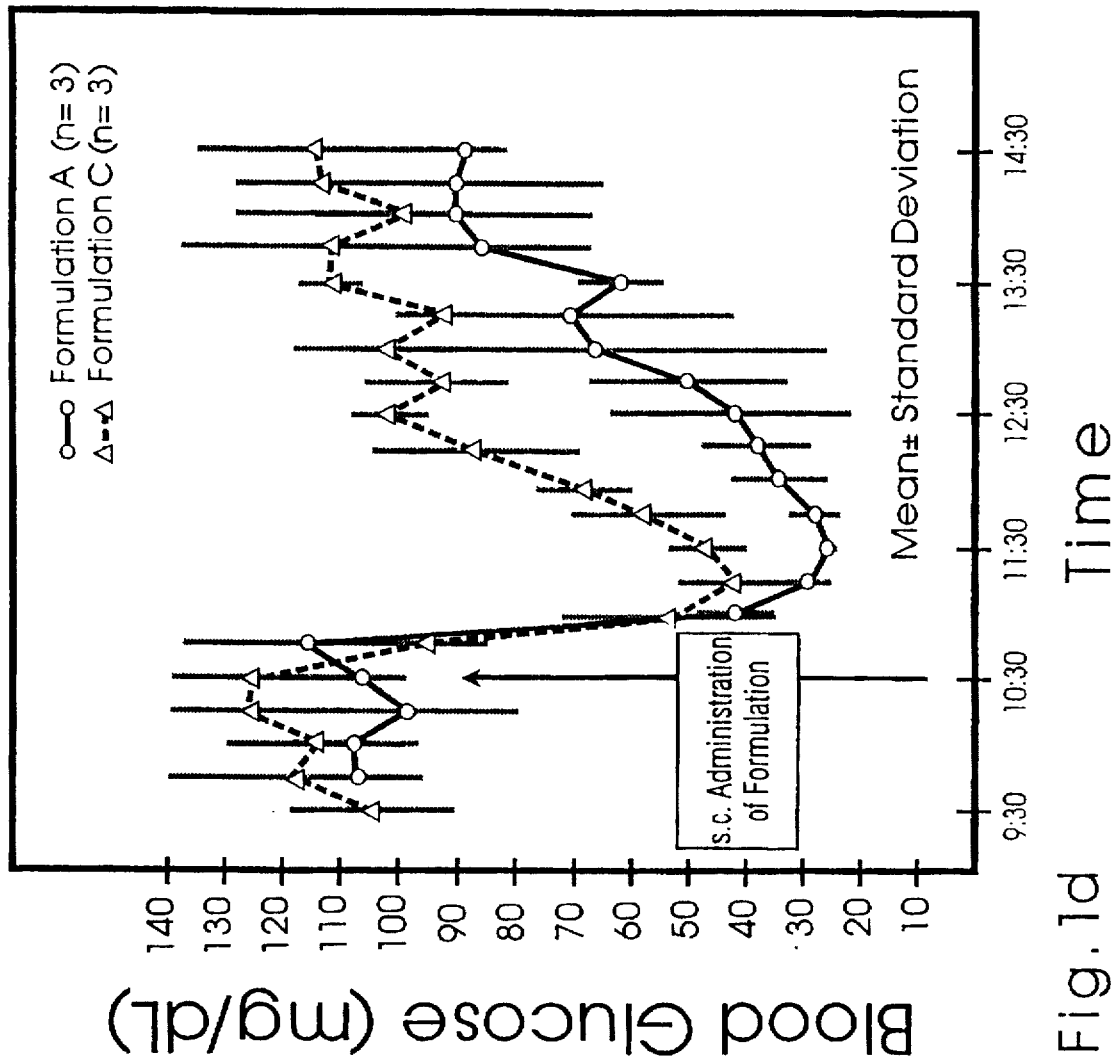

(ii) Moreover, it appears from FIGS. 1c and 1d that the inventive formulations containing soybean oil and unrefined coconut oil may be somewhat less potent than that containing fractionated liquid coconut oil in reducing the blood glucose concentration.

Figure 1E:
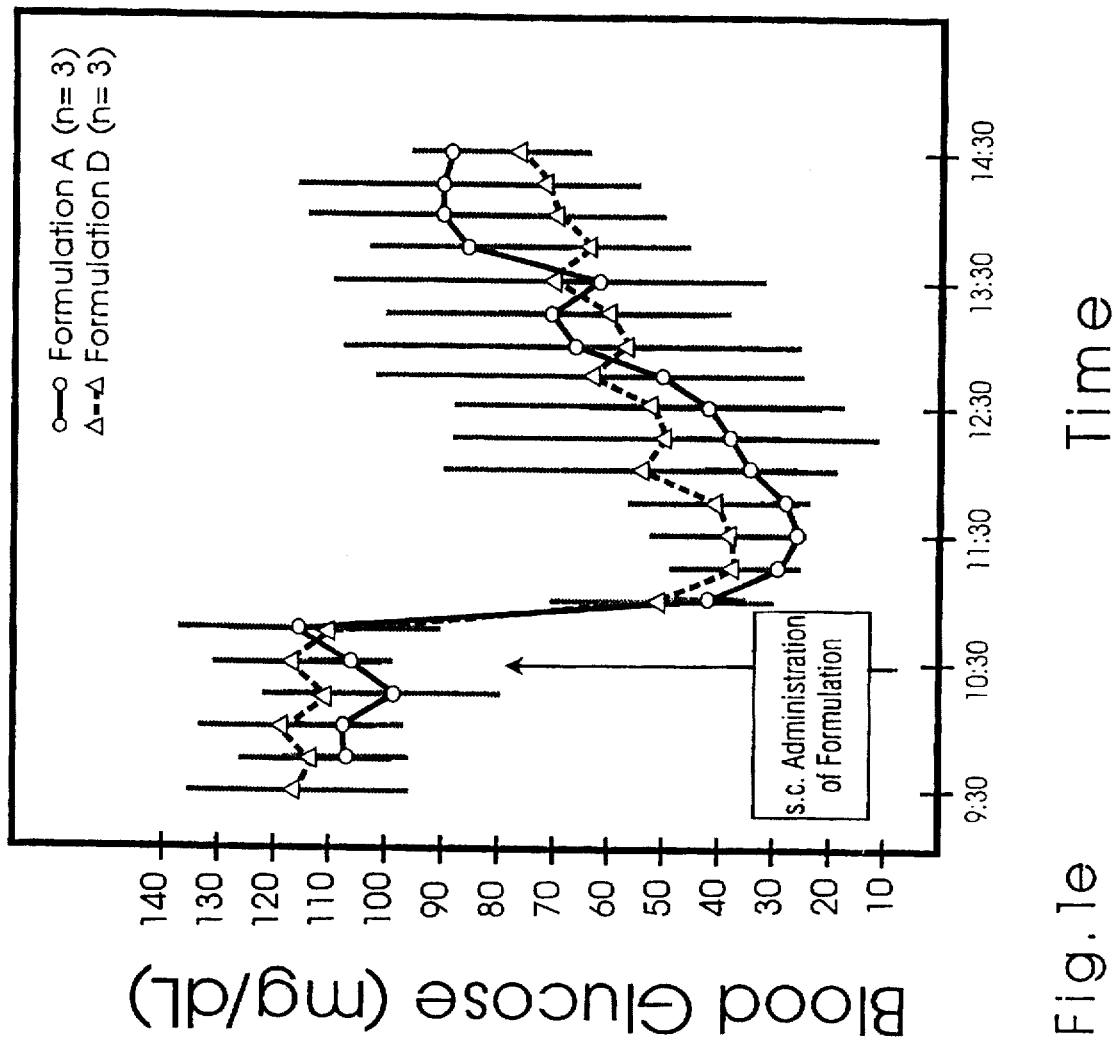
Figure 1F:
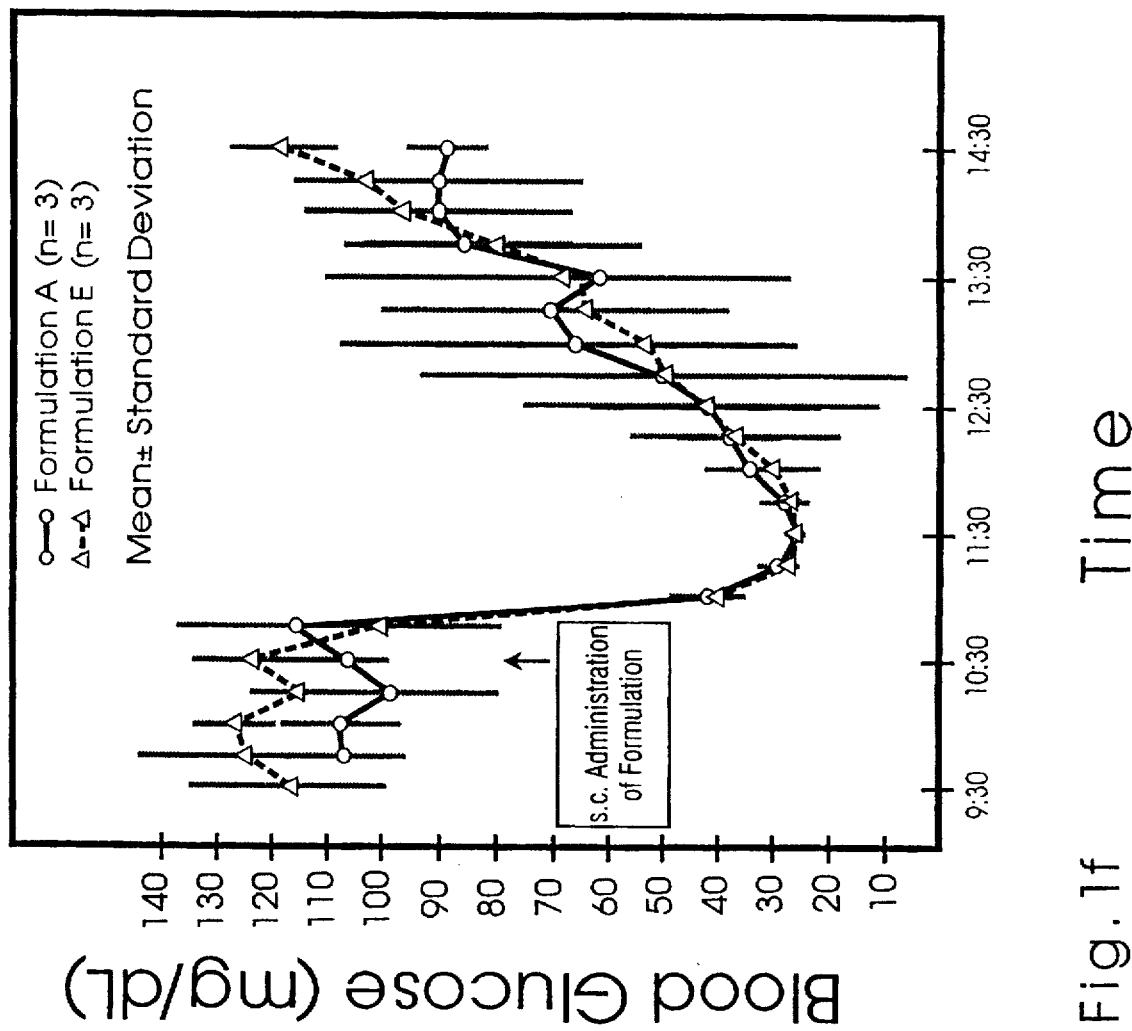

(iii) On the other hand, FIGS. 1e and 1f show that the inventive formulations containing olive oil instead of fractionated liquid coconut oil, or substituting Tween 80 for lecithin, have a potency in reducing the blood glucose concentration, similar to that demonstrated for Formulation A.

EXAMPLE 2

Figure 1G:
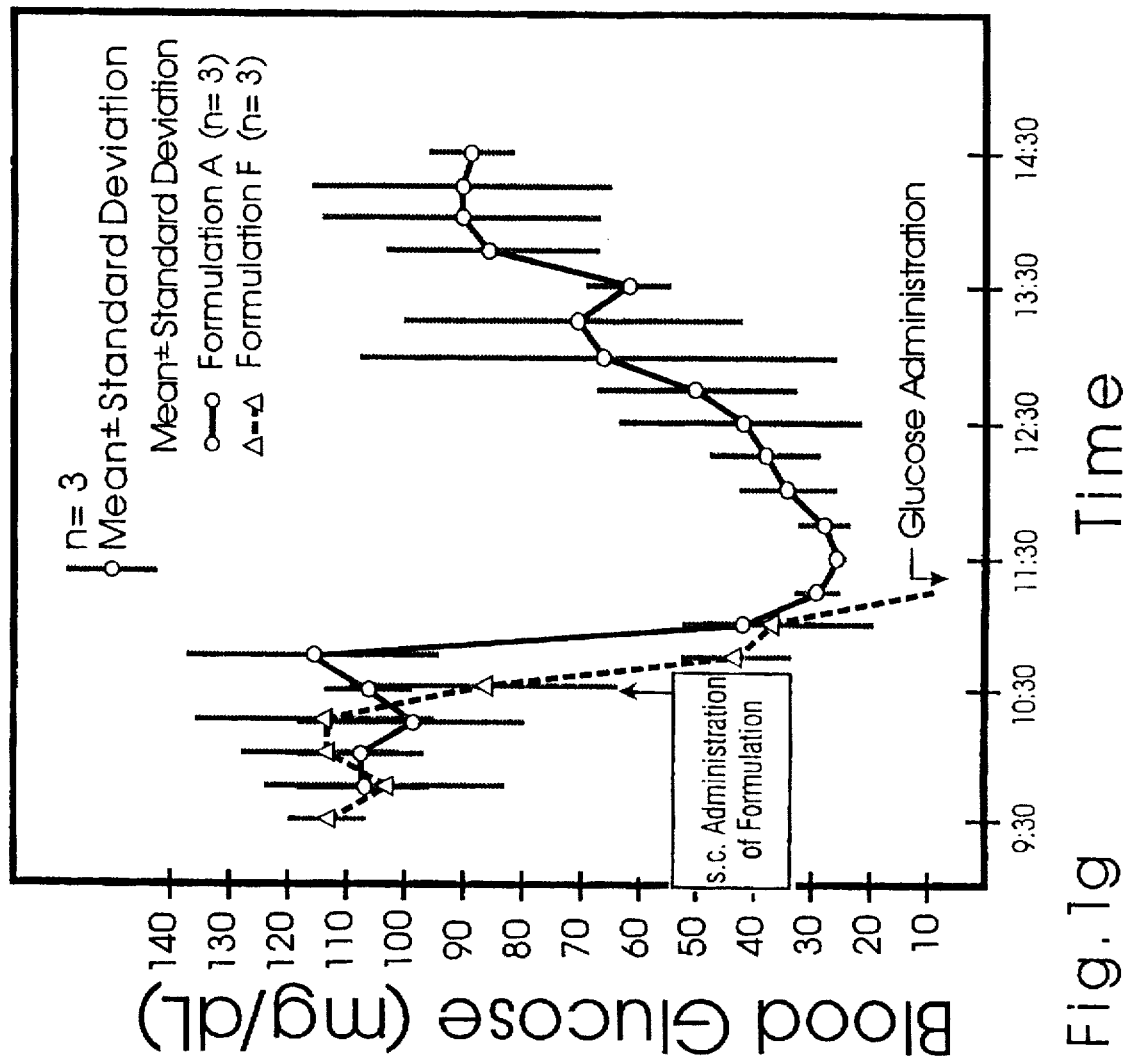

Working under the conditions described in Example 1, above, Formulation F in an amount equivalent to 1 iu insulin was used. After 60 minutes, it was found that all three rabbits exhibited extreme hypoglycemia, in which blood glucose could not be detected (lower limit of detection=25 mg/dl), see FIG. 1g. The experiment was terminated and the rabbits were administered glucose parenterally, resulting in the recovery of all three rabbits after 30–60 minutes. It thus appears that Formulation F demonstrated the highest insulin potency of all the exemplified formulations.

In a further experiment, a volume of Formulation F containing 0.5 iu insulin, on injection under similar conditions in two rabbits gave comparable results. This result appears to indicate that Formulation F is at least twice as potent as both Formulation A and Actrapid HM.

EXAMPLE 3

TRANSDERMAL ADMINISTRATION OF INSULIN TO HEALTHY RABBITS

Method

A transdermal dosage form was prepared by absorbing Formulation A (2.5 ml) onto a matrix consisting of four layers of absorbent paper towel cut into a circle of approximately 52 mm diameter and having a surface area of about 18 $cm^2$. The formulation contained 60 iu/ml insulin and was prepared one day prior to the study. The matrix was attached to a lightweight curved plastic support by means of an intermediate adhesive layer, and the composite placed on the inner side of the test animal's left ear so that the matrix contacted the untreated skin surface, the composite being taped to the ear for the duration of the experiment.

The four rabbits used were approximately six months old and weighed about 5–6 kg each. They were fasted overnight prior to the experiment but had free access to water, and also had free access to water during the study, but no food. In the hour preceding administration the blood glucose concentrations were determined every 20 minutes, i.e. three times. After administration, the blood glucose concentration was determined every 15 minutes during the next 8 hours. This study was denoted "TDD Insulin". A week later, a similar study was carried out on three rabbits of the same age and size, but replacing the Actrapid MH solution in Formulation A by water only; this is the vehicle control study, denoted "TDD VC".

Results

In the vehicle control study, the blood glucose concentration did not vary significantly from around 126 mg/dl throughout the study. In the "TDD Insulin" study, the blood glucose concentration decreased continuously throughout the study, in all test animals, and during the eighth hour averaged about 50 mg/dl, a reduction of 62% (see FIG. 2).

Conclusions

Figure 2:
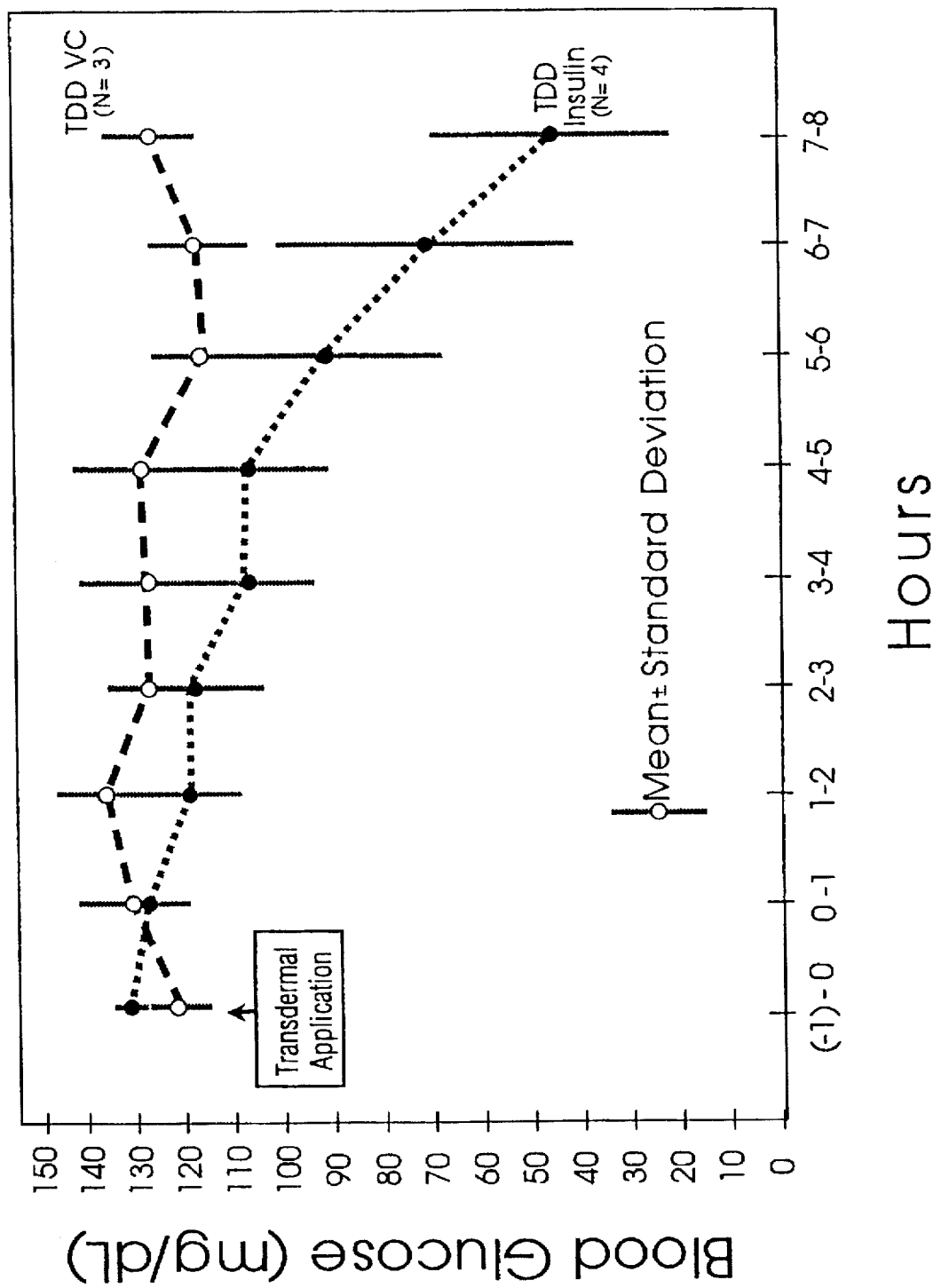
FIG. 2 depicts graphically the results of a study in which a formulation according to an embodiment of the invention is administered to healthy rabbits transdermally.

The dosage form containing Formulation A in accordance with the invention lowered the blood glucose concentration in healthy rabbits continuously for the 8-hour duration of the study. Moreover, a comparison of FIGS. 1a and 2 shows that the insulin penetrates the skin throughout this 8-hour period, having regard to the fact that in the case of FIG. 1a it is seen that approximately one hour after reaching the minimum glucose concentration, this then rises almost without interruption for the duration of the subcutaneous injection study.

EXAMPLE 4

TRANSDERMAL ADMINISTRATION OF INSULIN TO A HEALTHY HUMAN DURING FOOD DEPRIVATION

Method

This study was conducted on a healthy human male subject aged 43 years and weighing 65 kg, following overnight fasting and during food deprivation. During a period of two hours prior to application of the dosage form which was the matrix containing Formulation A described in Example 3, blood glucose concentration was determined every 30 minutes. The matrix was placed in a Hill Top Chamber (Registered Trade Mark of the Hill Top Companies) having a chamber diameter of 52.34 mm. The dosage form was secured to the inner upper right forearm with Durapore (Registered Trade Mark of 3M Personal Care Products) cloth tape, after which blood glucose concentrations were determined every 30 minutes during the first 90 minutes and every 15 minutes thereafter. After the dosage form had been in place 6.25 hours, the subject ate a bagel (130 g) and drank a cup of tea with 3 teaspoons of sugar; after a further 15 minutes the subject drank another cup of tea with 3 teaspoons of sugar. A week later the same study was conducted in absence of the dosage form; this was the control study.

Results

Figure 3:
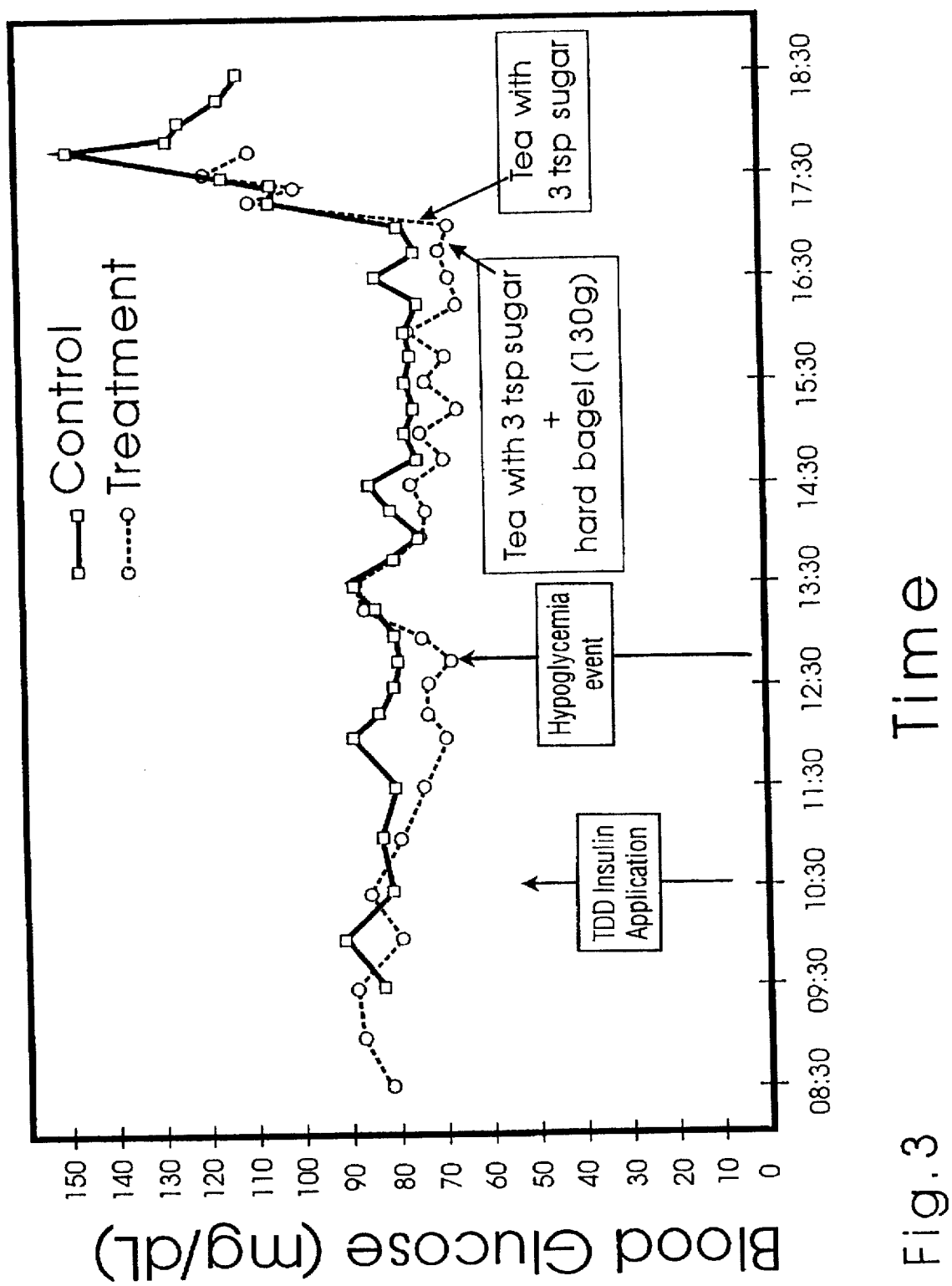
FIGS. 3, 4a and 4b depict graphically the results of studies using formulations according to embodiments of the invention.

These are shown graphically in FIG. 3. After the transdermal dosage form was applied, blood glucose concentrations decreased until the subject experienced an autonomous hypoglycemic event after which blood glucose concentration increased (Somogyi phenomenon) for the next 45 minutes and then decreased until after the subject drank the second cup of tea with 3 teaspoons of sugar. During transdermal administration blood glucose concentrations were consistently lower than the control, with the exception of the period of the Somogyi phenomenon during which time they were the same; moreover the blood glucose concentrations were on 9 occasions less than 69 mg/dl, whereas in the control study such concentration fell once only below 75 mg/dl. Following the food and sugar ingestion, the highest blood sugar concentration observed in the control study was 148 mg/dl, compared with only 119 mg/dl in the transdermal administration study. Furthermore, in the transdermal study, blood glucose concentration started to decrease between 30 and 60 minutes following application of the transdermal dosage form containing insulin.

Conclusions

The results of this study show that transdermal administration of insulin according to the invention decreases blood glucose concentrations in a healthy human subject for at least 7.25 hours.

EXAMPLE 5

TRANSDERMAL ADMINISTRATION OF INSULIN TO A HEALTHY HUMAN DURING FOOD DEPRIVATION AND FOOD CONSUMPTION

Method

This study was conducted on a healthy human male subject aged 43 years and weighing 65 kg, following overnight fasting. The dosage form was prepared and applied as in Example 4, after which blood glucose concentrations were determined every 15 minutes; and the transdermal and control studies were conducted one week apart. After the dosage form had been in place 90 minutes, the subject ate a bagel (130 g) and drank a cup of tea with 6 teaspoons of sugar; after 4 more hours the dosage form was removed, the site of application was cleaned and the subject drank (in the transdermal study only) another cup of tea with 6 teaspoons of sugar. The study was continued a 60 minutes, blood glucose concentrations being determined every 15 minutes.

Results

Figure 4A:
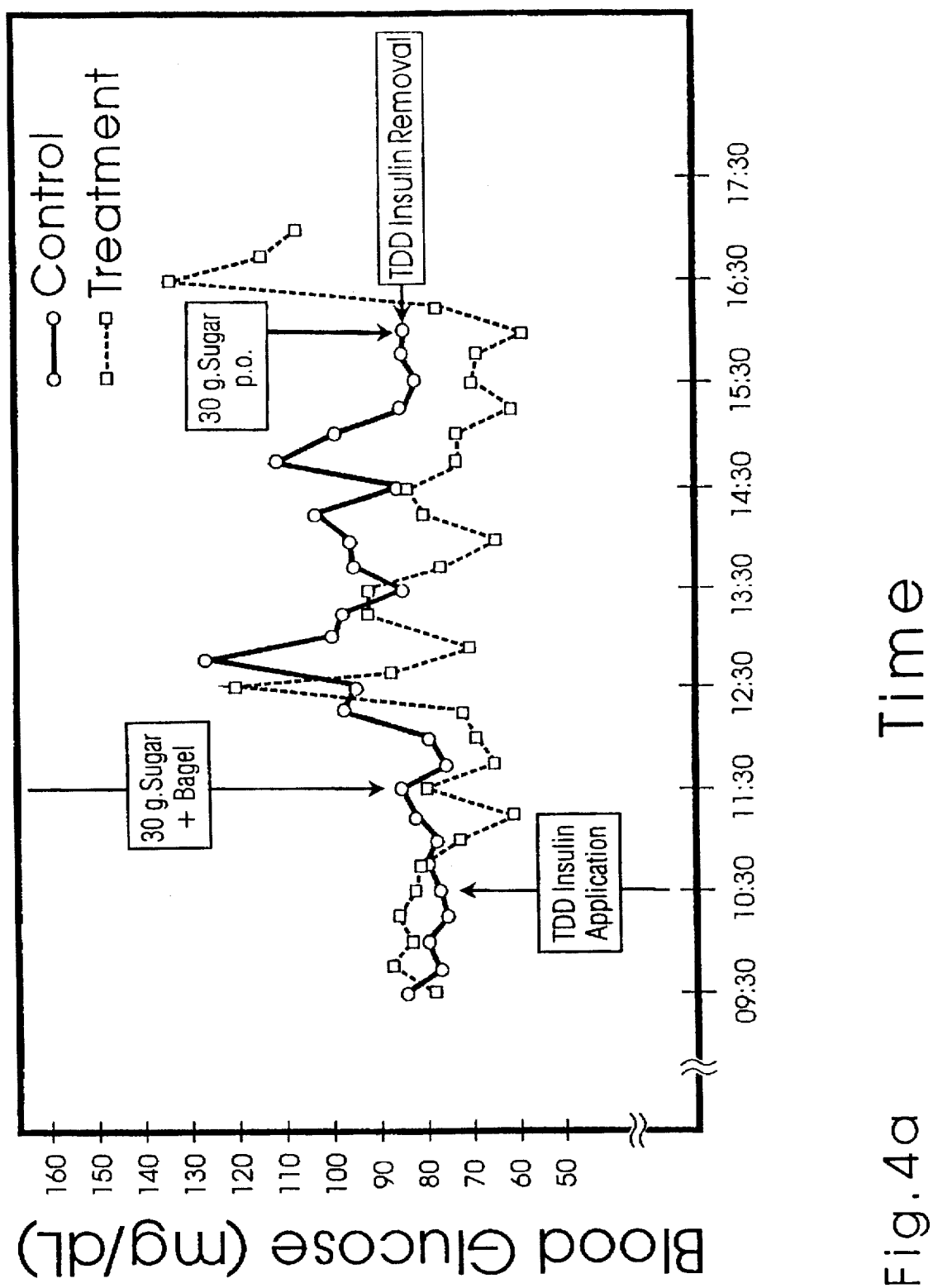

These are shown graphically in FIG. 4a. After the transdermal dosage form was applied, blood glucose concentrations decreased for the most part, compared with the control. Furthermore, blood glucose concentration started to decrease 30 minutes following application of the transdermal dosage form containing insulin.

Conclusions

The results of this study show that transdermal administration of insulin according to the invention decreases blood glucose concentrations in a healthy human subject for the major part of the duration of the study during both food deprivation and food consumption.

Figure 4B:
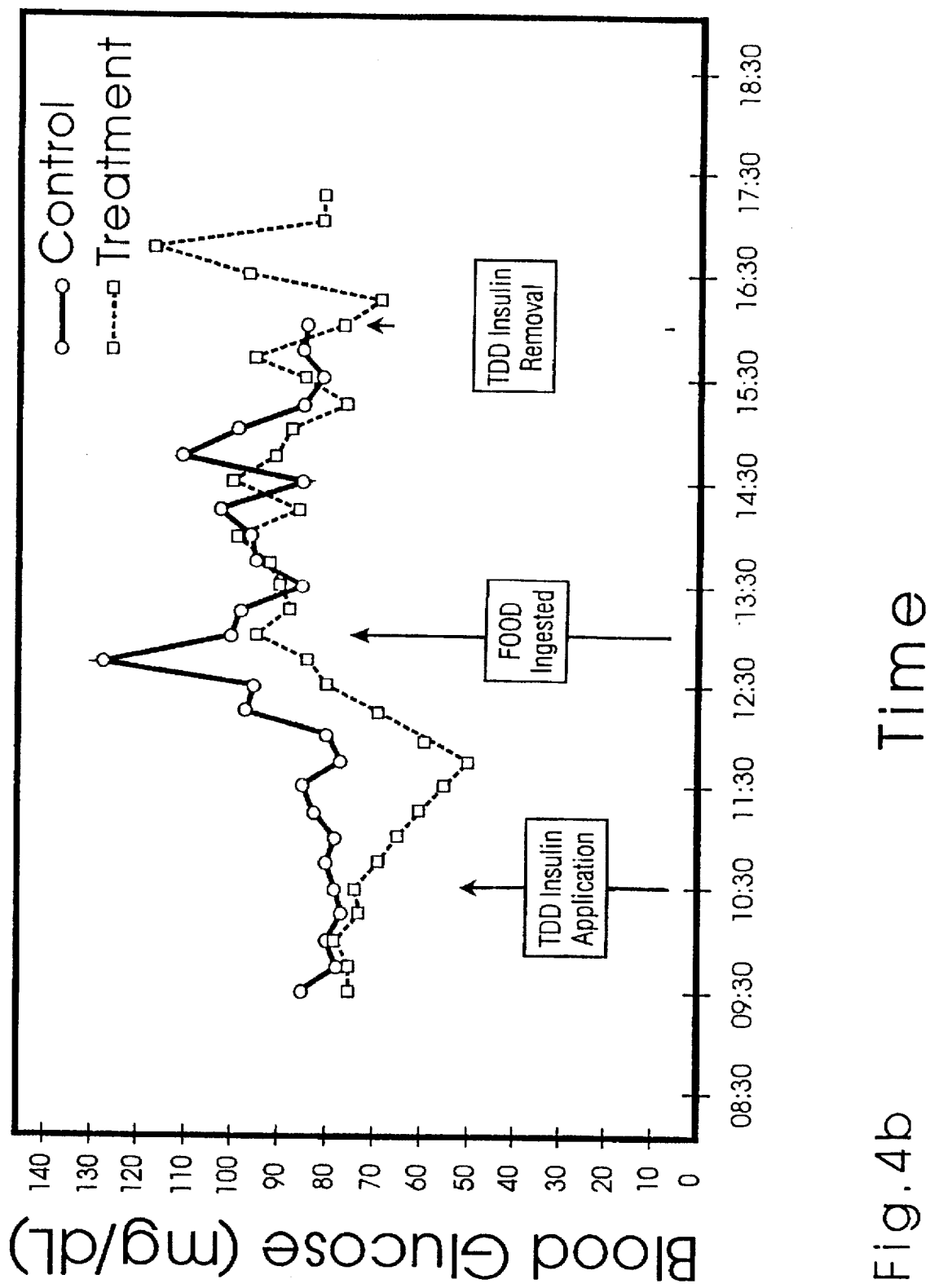

When the method of Example 5 was applied using the same transdermal dosage Form containing Formulation F instead of Formulation A, results are depicted graphically in FIG. 4b. It is seen that the blood glucose level fell to 50 mg/dl after 90 minutes and did not exceed 100 mg/dl during the period of transdermal administration (cf control maximum about 130 mg/dl). Even after ingestion of the second cup of tea on termination of transdermal administration, the glucose concentration increased to only 117 mg/dl. This study confirms one of the implicit findings of the experiments on rabbits reported above, namely, that by altering the nature of the vehicle and/or the emulsifier of the formulations within the concept of the present invention, it is possible to alter the potency of the administered insulin.

EXAMPLE 6

TRANSDERMAL ADMINISTRATION OF INSULIN TO A TYPE I INSULIN-DEPENDENT DIABETIC PATIENT

Method

This study was conducted on a Type-I insulin-dependent 11-year old male patient weighing about 32 kg, who received his regular insulin injection in the evening prior to the study, but no injections of insulin during the study. Prior to commencing the study, the blood glucose concentration was determined twice, following which the transdermal dosage form described in Example 5 (containing Formulation A) was applied. Blood glucose was determined after 30 minutes had elapsed, then every 15 minutes. At 90 minutes after commencement, the patient ate a chocolate-coated caramel wafer (28 g).

Results

Figure 5:
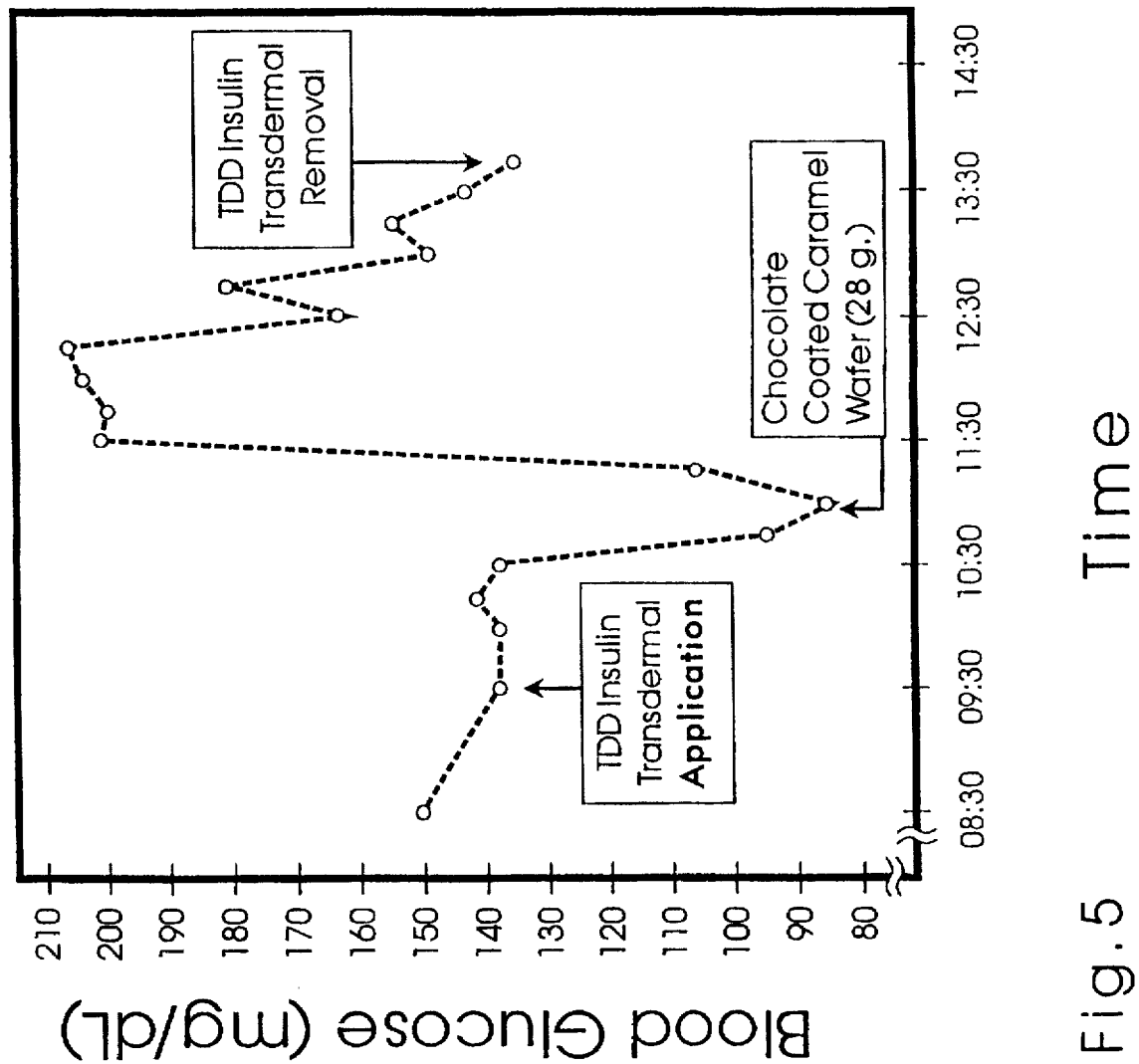
FIG. 5 depicts graphically the results of a study using a formulation according to an embodiment of the invention which is administered to a Type-I insulin-dependent diabetic patient transdermally.

Results are depicted graphically in FIG. 5. Prior to application of the transdermal dosage form the patient's blood glucose concentration was 140 mg/dl, and had decreased to 85 mg/dl (i.e. a 39% decrease) after 90 minutes.

Following ingestion of the food as stated the blood glucose concentration rose to 206 mg/dl during 75 minutes and then fell to 135 mg/dl (a reduction of 35%) in the course of the next 90 minutes.

Conclusions

The above results indicate that in a Type-I insulin-dependent diabetic patient, blood glucose concentrations can be lowered by use of a transdermal dosage form containing insulin in the form of a pharmaceutical formulation within the concept of the present invention.

EXAMPLE 7

When Formulation AA (prepared with sonication) was tested in one healthy male rabbit in a similar manner to that described in Example 1, results were obtained which were apparently somewhat better than when Formulation A (prepared without sonication) was used.

EXAMPLE 8

Formulations G and H were separately tested by subcutaneous administration to two healthy rabbits, one male and one female (i.e. two rabbits per formulation), after overnight fasting, as described above. 45 minutes after subcutaneous injection of 1 iu insulin, blood glucose was undetectable and the rabbits exhibited severe hypoglycemic symptoms. The experiment was terminated and the rabbits received glucose parenterally; they had recovered 30–60 minutes thereafter.

In the previous Examples (1–8), the insulin preparation marketed as Actrapid (R) HM was kept at ambient temperature for one month prior to formulation in accordance with the pretreatment feature of the present invention. In the following Examples (9–19), the commercial insulin preparations were kept at 37° C. for 30 days prior to formulation in accordance with the present invention. In these Examples, a modified glucose tolerance curve was used as the experimental design. The studies were conducted on a healthy male human, age 43 years and weighing 65 kg, following overnight fasting and food deprivation, from 9.00 to 16.30, during which period blood glucose concentrations were determined every 15 minutes. 2.5 hours after the study began the subject drank 150 ml of a lukewarm solution of tea containing 65 g sugar (1 g/kg body weight).

EXAMPLE 9

(a) "Glucose tolerance" curve in a healthy subject

Figure 8:
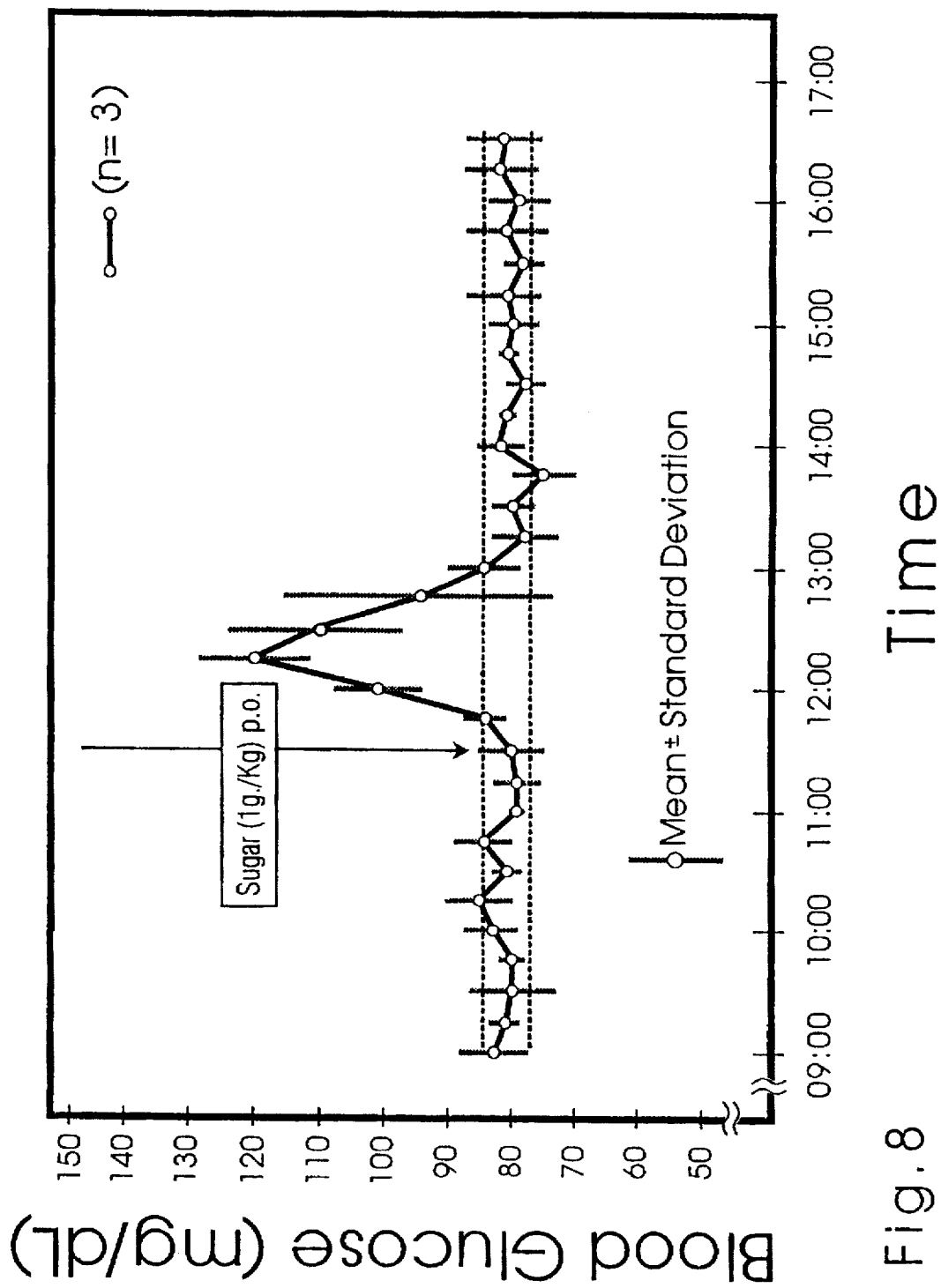
FIG. 8 depicts a modified glucose tolerance curve for a healthy subject.

On 3 separate occasions, the glucose tolerance test was performed on the subject. The results of these tests are presented in FIG. 8. During the 2.5 hours prior to ingestion of the sugar solution, blood glucose concentrations averaged 81 mg/dl. After drinking the sugar solution, blood glucose increased within 45 minutes to a peak of 120 mg/dl, i.e. +48%, and then gradually decreased within the next 45 minutes to values similar to those prior to the sugar challenge, and remained at these values until the end of the experiment (FIG. 8). This study will be referred to as the "control" in Examples 10–19.

In Examples 10–19, the above glucose tolerance test was modified in that one hour after the study commenced and 1.5 hours prior to the sugar challenge, a transdermal dosage form containing insulin was applied to the subject's inner upper right forearm, and maintained there for the duration of the study with an elastic Uriel(R) armband. Formulation A was slightly modified in that it contained the insulin, pretreated at 37° C. for 30 days, to which approximately 20 mg of m-cresol was added to a whole bottle of Actrapid(R) HM insulin preparation (about 10 ml), and gently mixed by hand. 10 ml were then withdrawn from this bottle and 1600 mg of pure soya lecithin powder (as previously described) were then mixed at 35° C. for 105 minutes, after which 6 ml of fractionated liquid coconut oil (previously described) was added and mixing was continued for a further 150 minutes at 35° C. The resulting mixture contained approximately 62.5 iu of insulin per ml. 3 ml were then absorbed onto the matrix and placed in the Hilltop (R) chamber as previously described. Thus, each such dosage form contained approximately 187.5 iu of insulin.

(b) Transdermal insulin administration in a healthy subject—Formulation A

Figure 9:
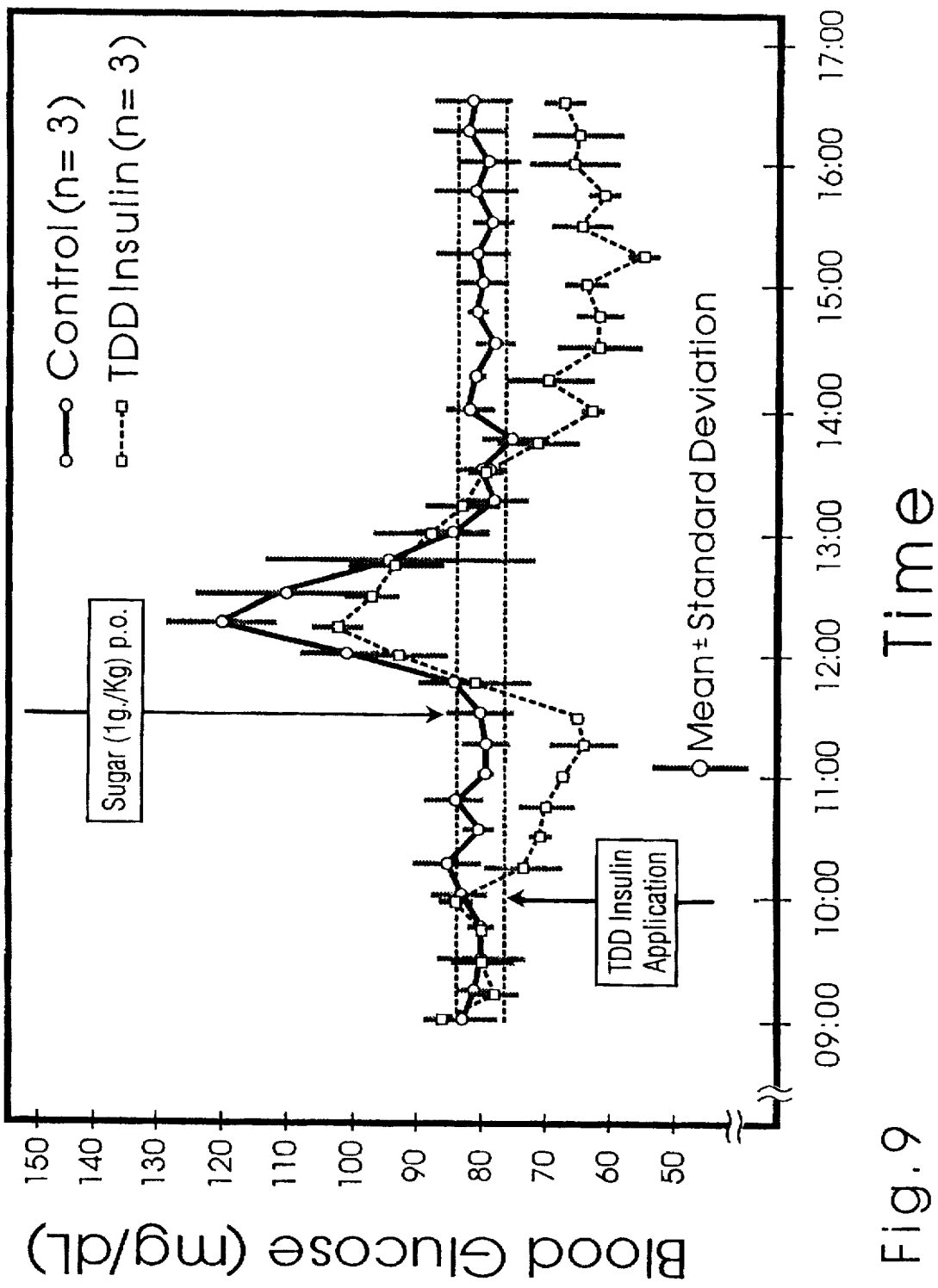
FIG. 9 depicts graphically the results of studies using a formulation according to an embodiment of the invention.

Modified formulation A was tested on the healthy subject on 3 different occasions. Results of this study were compared to the control experiment (Example 9(a)), and presented in FIG. 9. Prior to administration of the transdermal dosage form ("TDD insulin"), blood glucose level was similar to that of the control study. However, the blood glucose level started to decline within the first 15 minutes after the dosage form was applied and continued to fall until the sugar challenge. Prior to the sugar challenge, blood glucose fell to an average of 65 mg/dl (−21%); 45 minutes after the sugar challenge, blood glucose increased to its peak of an average of 102 mg/dl (i.e. 15% less than control), and then gradually fell, and averaged 65 mg/dl over the final 3 hours of the study, being considerably lower than the control (FIG. 9). These results demonstrated that insulin was continuously absorbed from the transdermal dosage form over the 6.5 hours of this experiment, resulting in lower glucose levels compared with the control over most of this time period.

EXAMPLE 10

Figure 10:
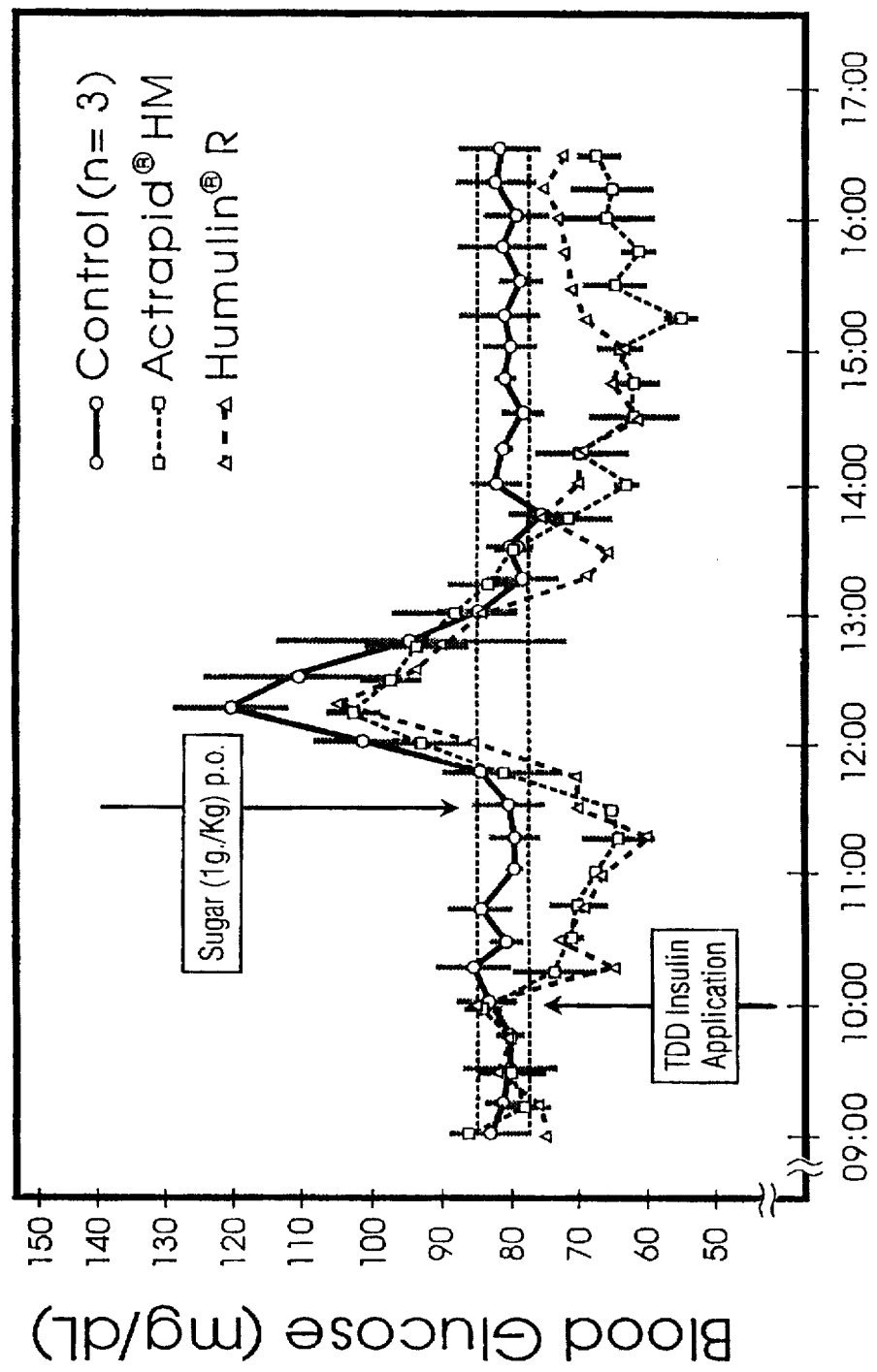
FIG. 10 compares the results of studies in which two different commercially available insulin preparations are used to make separate formulations according to embodiments of the invention.

Transdermal insulin administration in a healthy subject using formulations containing different proprietary preparations of insulin The modified formulation A was prepared as in Example 9 with the exception that instead of using the pretreated Actrapid (R) HM preparation, a similar aqueous solution of Humulin (R) R (regular human insulin of recombinant DNA origin—Eli Lilly & Co.), which contained 100 iu insulin/ml, and 0.25% m-cresol, which had been added as a preservative during manufacture. The Humulin (R) R preparation was pretreated in the same manner as the Actrapid (R) HM preparation, prior to its incorporation into the formulation, which was then tested under the conditions described in Example 9 for the Actrapid (R) HM preparation. The results of these tests are presented in FIG. 10, which shows comparison of the two insulin preparations with each other and with the control. It is observed that the two studies gave similar results, except that during the last 90 minutes of this experiment, the Humulin (R) R preparation did not give as low levels of glucose as the Actrapid (R) HM preparation, but the levels obtained with Humulin (R) R were still lower than the control.

Results of this study show that the present invention is not restricted to use of a particular proprietary preparation of insulin, but that various preparations of insulin may be used, in order to reduce blood glucose levels by transdermal administration.

EXAMPLE 11

Figure 11:
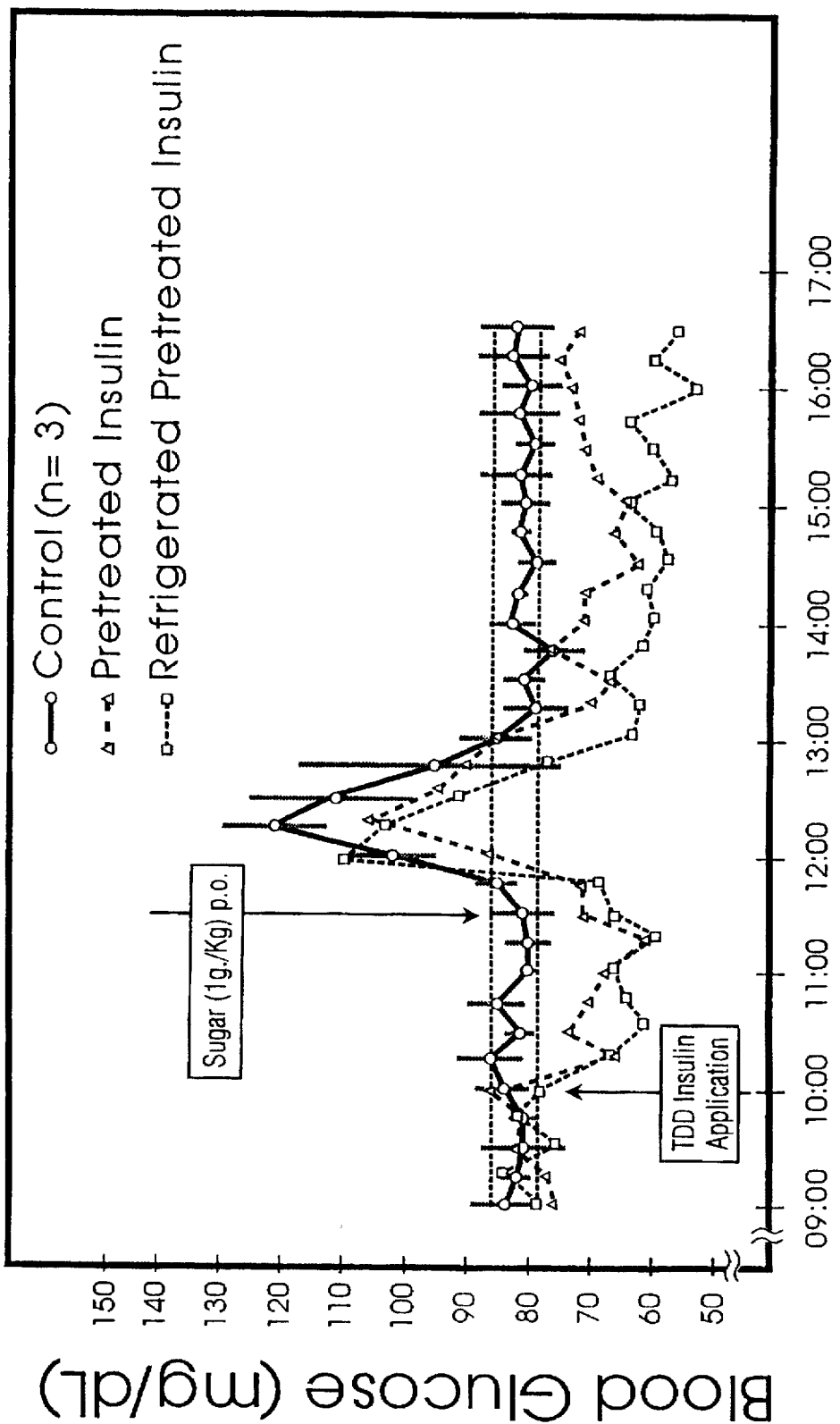
FIG. 11 illustrates the effect of refrigerating pretreated insulin on the activity of a formulation according to an embodiment of the invention.

Transdermal insulin administration in a healthy subject—effect of refrigeration of pretreated insulin The Humulin (R) R preparation was pretreated at 37° C. for 30 days, stored in a refrigerator at 2°–8° C. for 60 days, and then incorporated into modified Formulation A, and the dosage form was prepared. Results of this study, compared with pretreated, non-refrigerated material, and with the control, are presented in FIG. 11, and demonstrate that refrigeration after pretreatment does not diminish the activity of the formulation in accordance with the present invention and may even enhance the activity.

EXAMPLE 12

Figure 12:
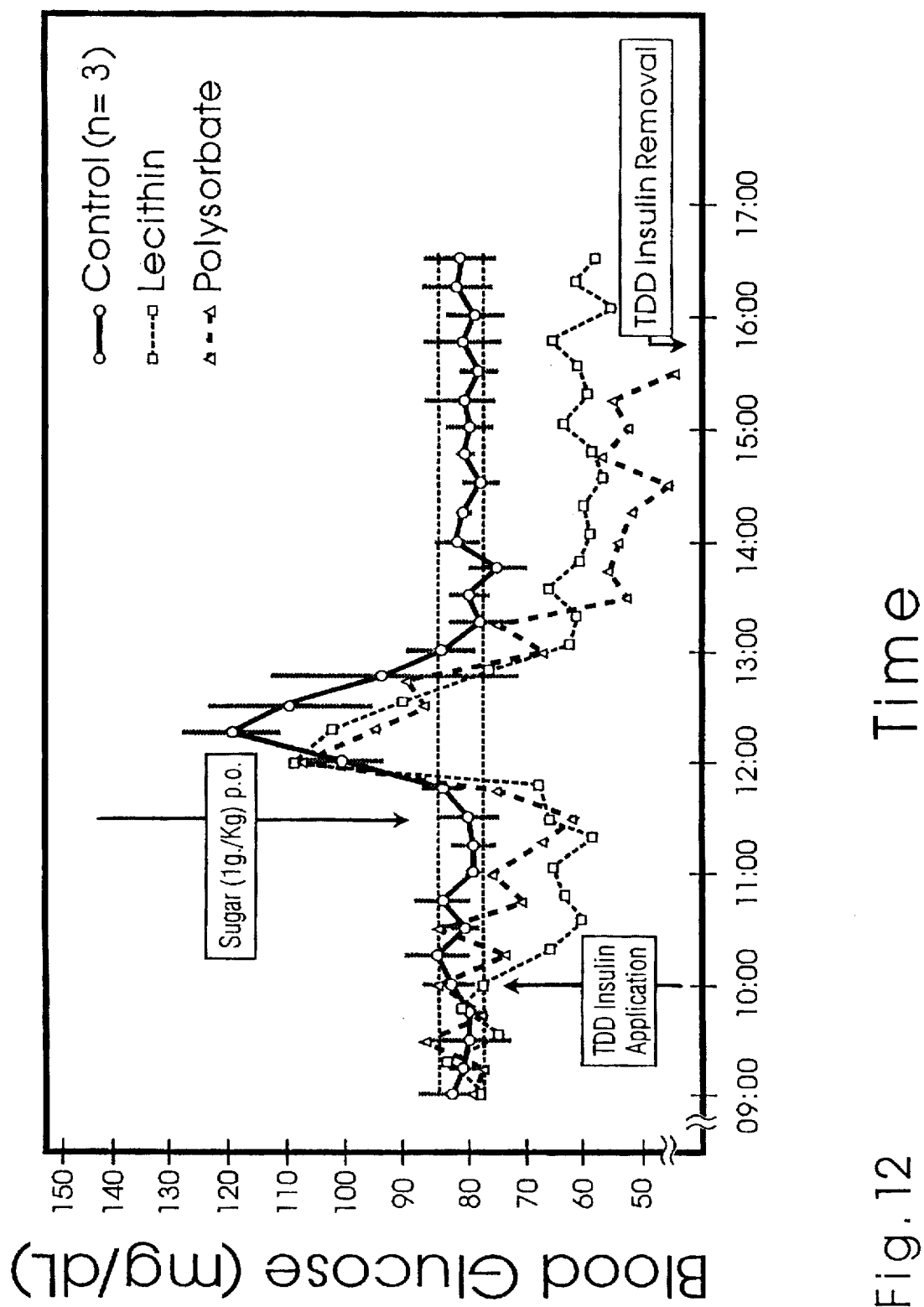
FIG. 12 compares the results of studies in which two different emulsifiers are used to make separate insulin formulations according to embodiments of the invention.

Transdermal insulin administration in a healthy subject—effect of identity of emulsifier The Humulin (R) R preparation was pretreated at 37° C. for 30 days, stored in a refrigerator at 2°–8° C. for 60 days, and then incorporated into modified Formulation E containing Tween 80. This modified formulation contained 48 iu/ml insulin, thus the dosage form contained 144 iu insulin, compared with 187.5 iu/ml insulin in modified formulation A (which contained lecithin as emulsifier). Results of testing the insulin dosage form containing modified formulations E and A (see Example 11) are compared in FIG. 12. There appears to be a delay in initiation of activity in formulation E, compared with formulation A; this may possibly be related to the fact that formulation E contained 23% less insulin/ml than formulation A. However, the blood glucose values soon after the sugar challenge appear to be very similar, but subsequently formulation E lowered the blood glucose concentration to a greater extent than formulation A. When the blood glucose fell to 44 mg/dl, the study was terminated (FIG. 12). Notwithstanding the initial delay in manifesting blood glucose lowering activity, by the end of the study the formulation containing Tween 80 evidently showed much more potency in this respect, than the formulation containing lecithin.

EXAMPLE 13

Transdermal insulin administration in a healthy subject—effect of oil phase

Figure 13:
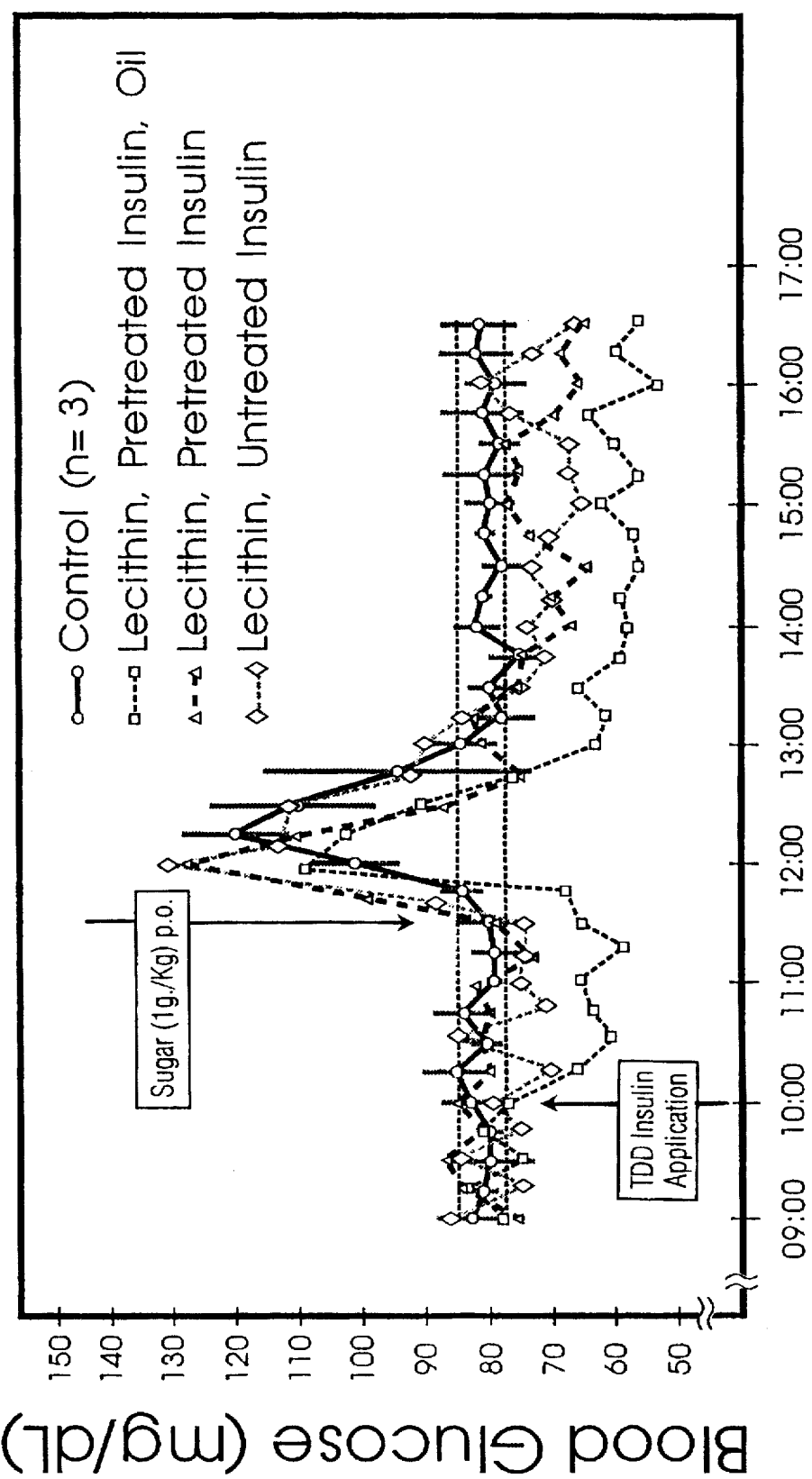
FIGS. 13 and 14 depict the results of studies in which insulin formulations according to embodiments of the invention are compared with the effect of omitting the oil phase from the formulations.

The first part of this study was conducted to determine the importance of the oil phase component in modified formulation A in transdermal administration of insulin, by omitting the oil phase in comparative formulations prepared from both pretreated and untreated formulations, in a manner similar to modified formulation A. All formulations were tested as previously described. Modified formulation A contained 187.5 iu, compared with 300 iu for the formulations from which the oil phase was omitted. The Humulin (R) R preparation was pretreated at 37° C. for 30 days, stored in a refrigerator at 2°–8° C. for 60 days, and then incorporated into the formulations, as in Example 12 (unless untreated insulin was used). Insulin absorption was significantly less when the oil phase was omitted (whether pretreated or untreated) from these dosage forms—notwithstanding that they contained considerably more insulin, than when oil phase was present, see FIG. 13. These results indicate the significant effect of the presence of oil phase in the formulation, in increasing the absorption of transdermally administered insulin.

Figure 14:
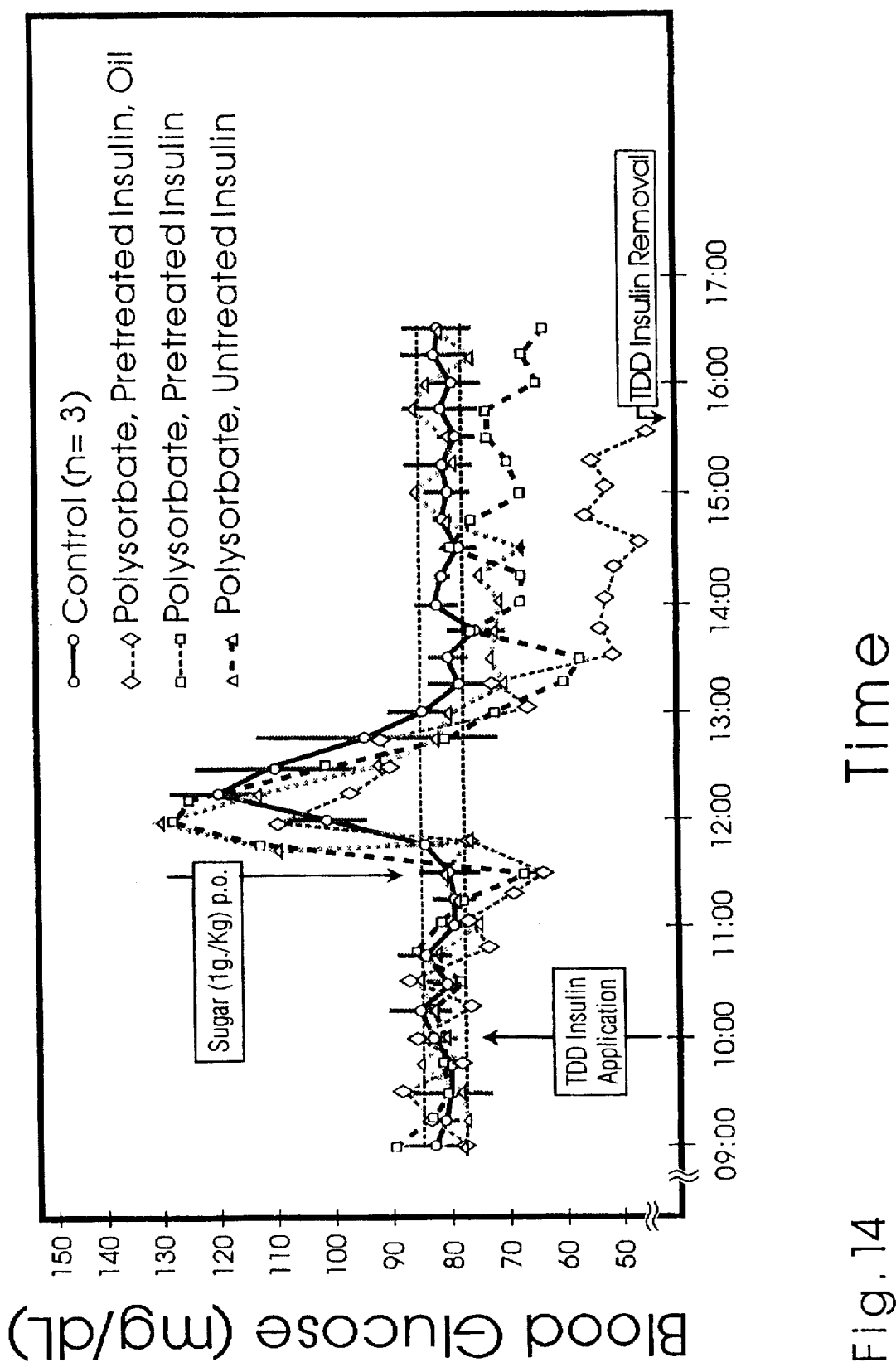

The second part of this study was conducted similarly to the first part, above, to determine the importance of the oil phase component in modified formulation E in transdermal administration of insulin. Modified formulation E contained 144 iu insulin, whereas when the oil phase was omitted the formulations contained 212 iu insulin. Results presented in FIG. 14 show that insulin absorption was initially somewhat greater in the formulation containing the oil phase than when this was omitted, but the most dramatic jump in the activity of the formulation containing oil phase occurred following the sugar challenge.

Thus, it may be concluded that the presence of the oil phase enhanced the glucose reducing activity of the transdermal formulations, whether the emulsifier was lecithin or Tween 80, and notwithstanding that the oil-containing formulations contained less insulin than the comparative formulations from which the oil phase had been omitted.

EXAMPLE 14

Transdermal insulin administration in a healthy subject—effect of pretreatment of the insulin The first part of this study was conducted to examine the effect of pretreating the Humulin (R) R at 37° C. for 30 days, prior to incorporation into modified Formulation A. Each ml of this insulin solution contained 100 iu insulin. The transdermal insulin dosage form containing 3 ml of the following four formulations was tested on separate days in a healthy subject:

(a) untreated Humulin (R) R, of which 3 ml contained 300 iu insulin;
(b) untreated Humulin (R) R, incorporated into modified Formulation A, of which 3 ml contained 187.5 iu insulin;
(c) pretreated Humulin (R) R, of which 3 ml contained 300 iu insulin;
(d) pretreated Humulin (R) R, incorporated into modified Formulation A (which was used in Example 10), of which 3 ml contained 187.5 iu insulin.

Figure 15:
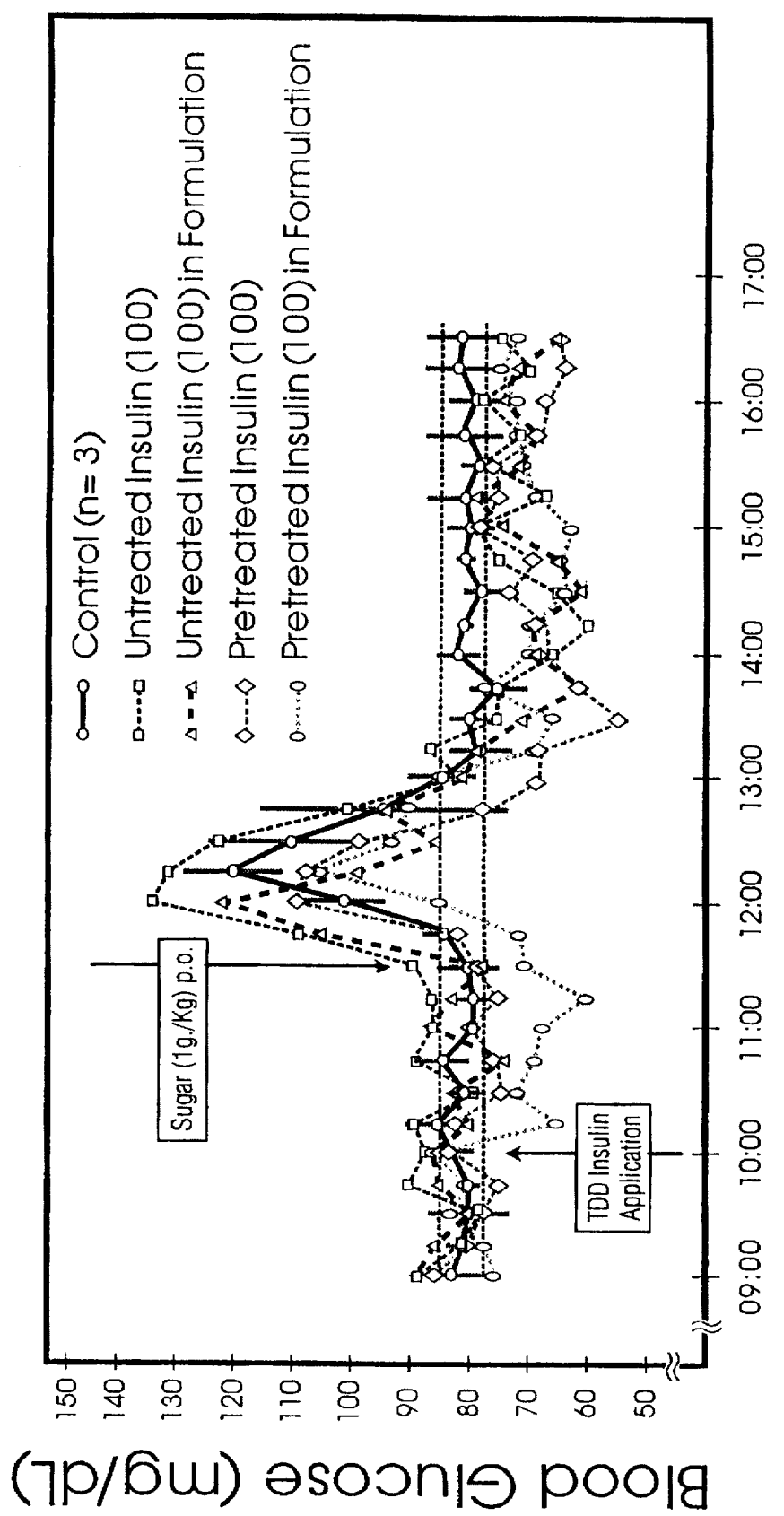
FIGS. 15 and 16 depict the results of studies in which formulations containing pretreated insulin are used, compared with pretreated insulin not in such formulation, and with non-pretreated insulin whether or not in such formulation.

Each of the above formulations (3 ml) was tested on a healthy human subject for reduction of the blood level of glucose. Effectivity of (a) was poor, but a slight improvement was shown by (b) or (c). However, (d) was by lap the most effective (FIG. 15).

Figure 16:
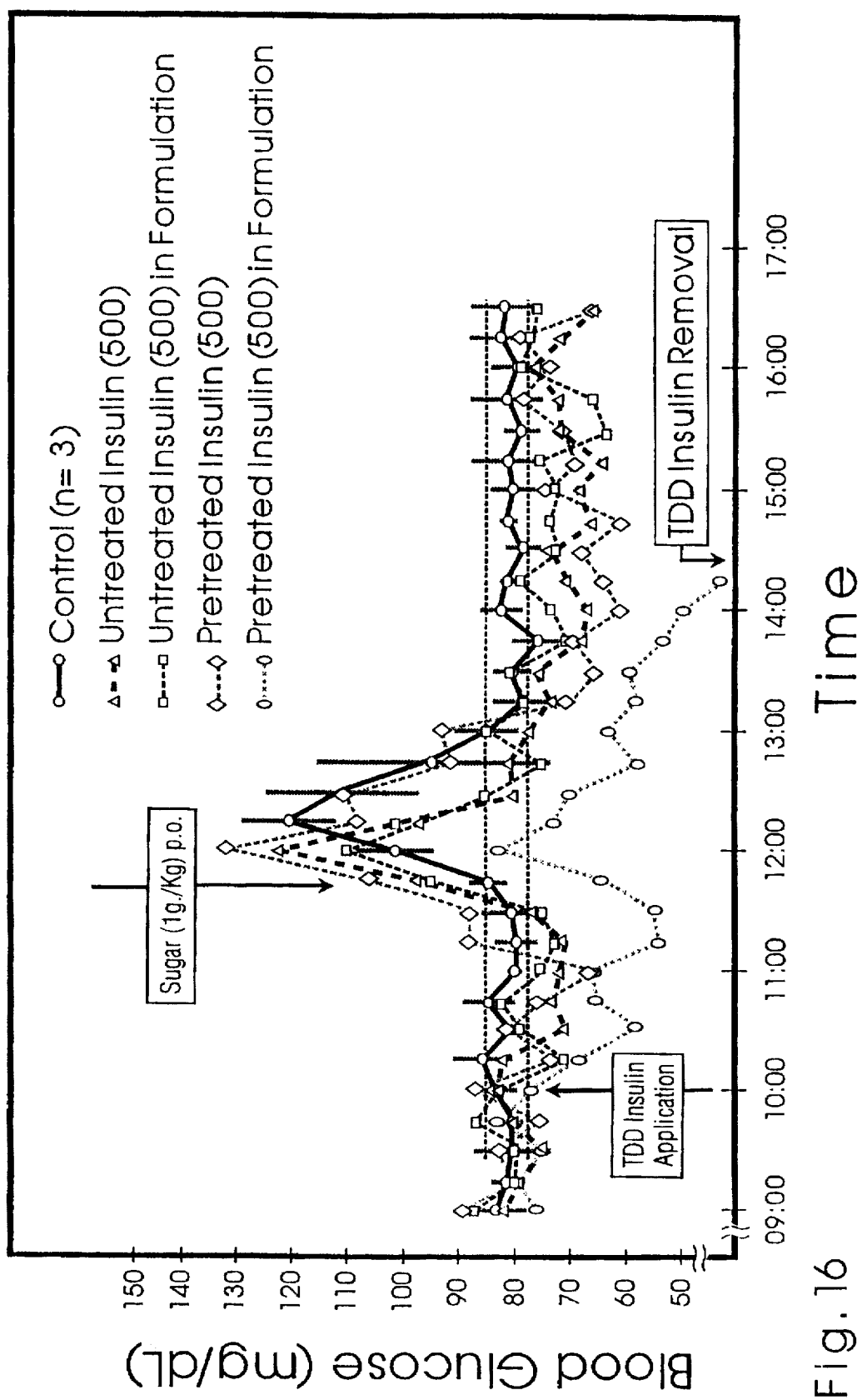

The second part of the study was similar to the first, except that Actrapid (R) HM insulin preparation, which contained 500 iu insulin/ml, was used in place of the Humulin (R) R preparation. The results were also similar to the first, with the exception that when using pretreated Actrapid (R) HM incorporated in modified Formulation A, the decrease in glucose blood concentration was so pronounced that the dosage form had to be removed from the subject about 2.75 hours after the sugar challenge, when the glucose concentration had dropped to 45 mg/dl (FIG. 16).

The results obtained in Examples 5 and 12–14 indicate that the most potent insulin delivery system contained pretreated insulin, together with emulsifier and oil phase.

In the following Examples 15–19, Actrapid (R) HM, in a concentration of either 100 or 500 iu/ml, was pretreated for 30 days at 37° C., prior to incorporation in modified Formulation A, and then tested for effectivity in reducing blood glucose concentration in a healthy subject.

EXAMPLE 15

Transdermal insulin administration in a healthy subject—effect of concentration

This study was conducted in order to determine the effect of insulin concentration on the reduction of blood glucose concentration, in the transdermal dosage form, in accordance with the invention.

In the first part of this study, the activity of such dosage form containing approximately 797 iu (265.6 iu/ml) insulin ("TDD insulin forte") was compared with that containing 187.5 iu (62.5 iu/ml) insulin from Example 9 ("TDD insulin"). Results are presented in FIG. 17.

Figure 17:
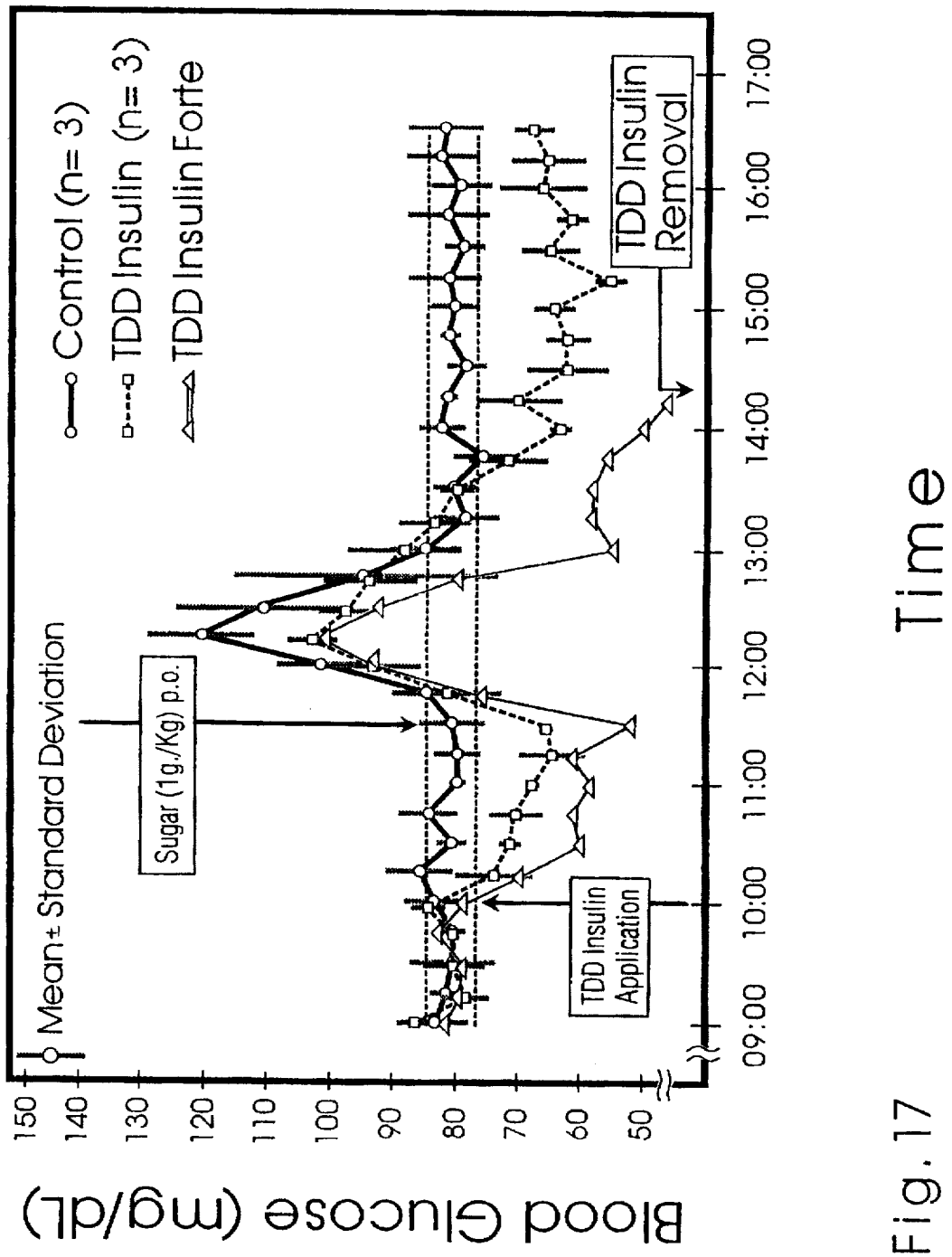
FIGS. 17, 18, 24 and 25 depict the results of studies on high dosage formulations containing insulin.

Blood glucose concentrations were more sharply reduced when using TDD insulin forte, than with TDD insulin; also, when using TDD insulin forte, the dosage form had to be removed when the glucose concentration had fallen to 45 mg/dl (FIG. 17).

Figure 18:
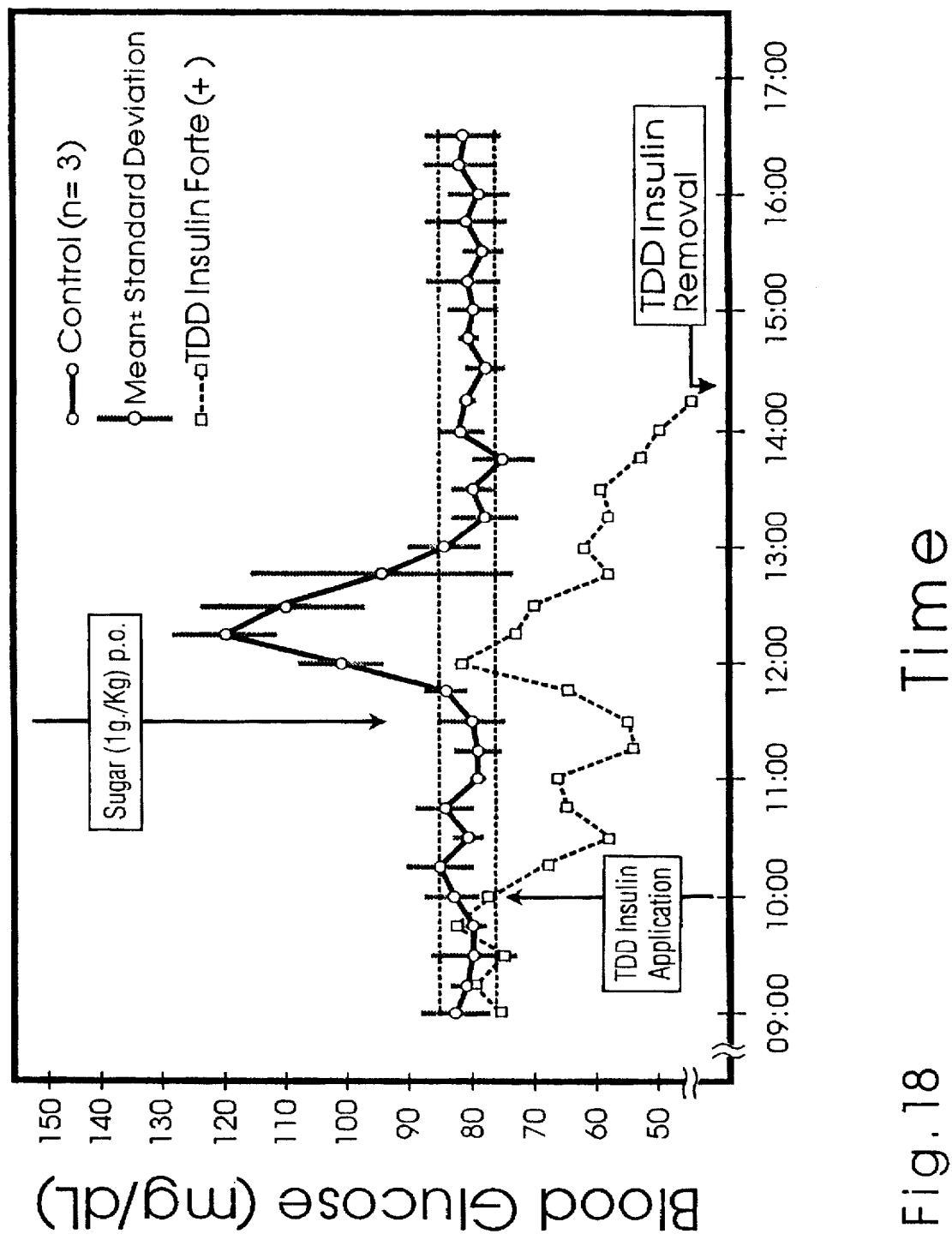

In the second part of the study, the activity of such dosage form containing approximately 937.5 iu (312.5 iu/ml) insulin ("TDD insulin forte(+)), was tested. Blood glucose levels were low throughout, after application of the transdermal dosage form. The highest blood glucose level during this period was 80 mg/dl, i.e. the peak after the sugar challenge, and the dosage form had to be removed when blood glucose concentration fell to 45 mg/dl (FIG. 18).

Results of this study indicate that the higher the insulin concentration in the transdermal insulin dosage form (when using identical volumes), the more effective it was in reducing blood glucose concentration.

EXAMPLE 16

Transdermal insulin administration in a healthy subject—effect of surface area

This study was conducted in order to determine the effect of surface area at the site of application, of the transdermal insulin dosage form, on the reduction of blood glucose concentration.

Figure 19:
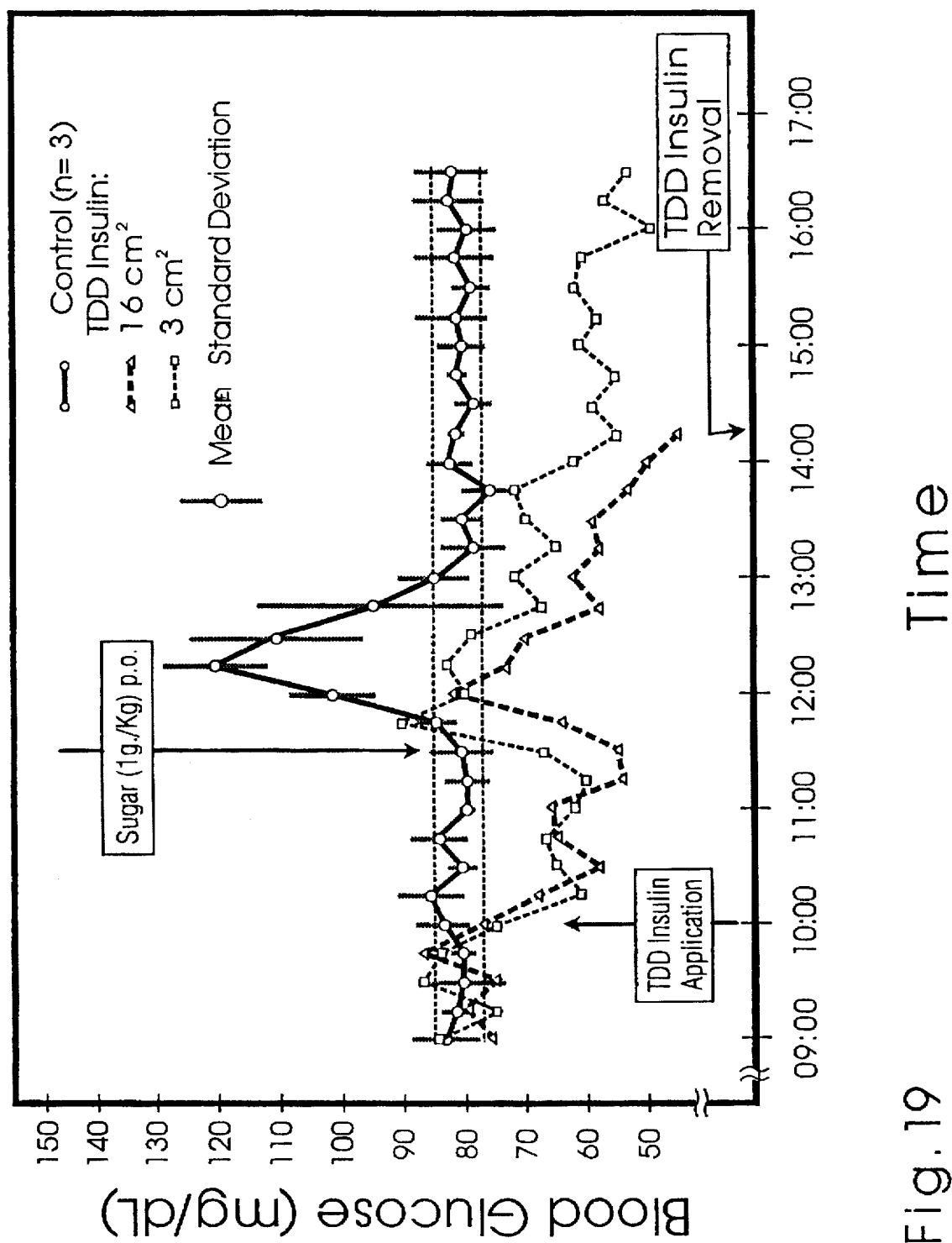
FIGS. 19 and 20 depict the effect of surface area and of site of administration, respectively, on the activity of transdermal insulin formulations.

0.3 ml of the modified formulation A from the second part of the previous Example (312.5 iu/ml) was absorbed onto the matrix (3 cm$^2$) and placed in a Hilltop Chamber (R) having a surface area of 3 cm$^2$ and thus contained 93.8 iu insulin. This dosage form was tested in the same manner as the one in the second part of the previous Example (TDD insulin forte (+)), which had a surface area of 16 cm$^2$, and the results compared in FIG. 19. After application of this transdermal dosage form, blood glucose values were lower than control but somewhat higher than those achieved with the transdermal dosage form having the greater surface area (FIG. 19). Although the surface area of the smaller (3 cm$^2$) dosage form was approximately 19% of the larger one (16 cm$^2$) and contained approximately 10% of the insulin quantity, the relative decrease in blood glucose was not so very different for the two. These results indicate that concentration was a more important factor than surface area in the transdermal dosage forms (c.f. Example 15).

EXAMPLE 17

Figure 20:
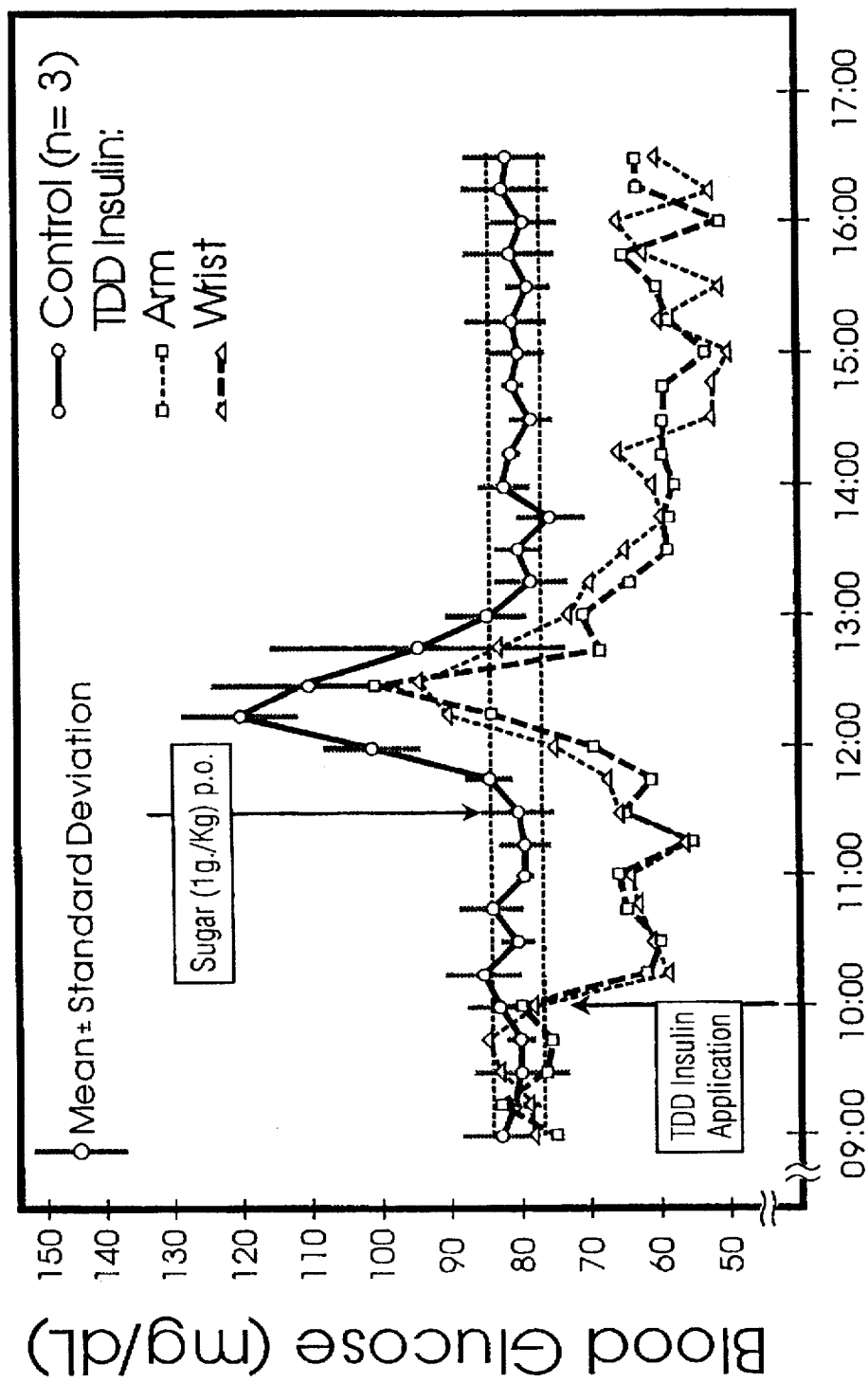

Transdermal insulin administration in a healthy subject—effect of site of application In previous Examples of transdermal administration of insulin to a healthy subject (and to a diabetic patient), the dosage form was placed on the upper right forearm ("Arm") and secured there for the duration of the study. The present study was conducted to determine whether application at a different site of the body could achieve similar results, and in particular the dosage form was applied to the wrist area of the inner lower right arm ("Wrist"). The formulations and the study protocol were as in Example 9. Results of the present study are compared with those of Example 9 (FIG. 20). Blood glucose levels throughout the experiment were similar to those of Example 9, indicating that the transdermal delivery of insulin is similar in the different sites of the body tested.

Taking together the results of the last three Examples, it may be concluded that the activity of the transdermal dosage form is very much concentration-dependent, somewhat dependent on area of application, and appears to be independent of the site of application.

EXAMPLE 18

Figure 21:
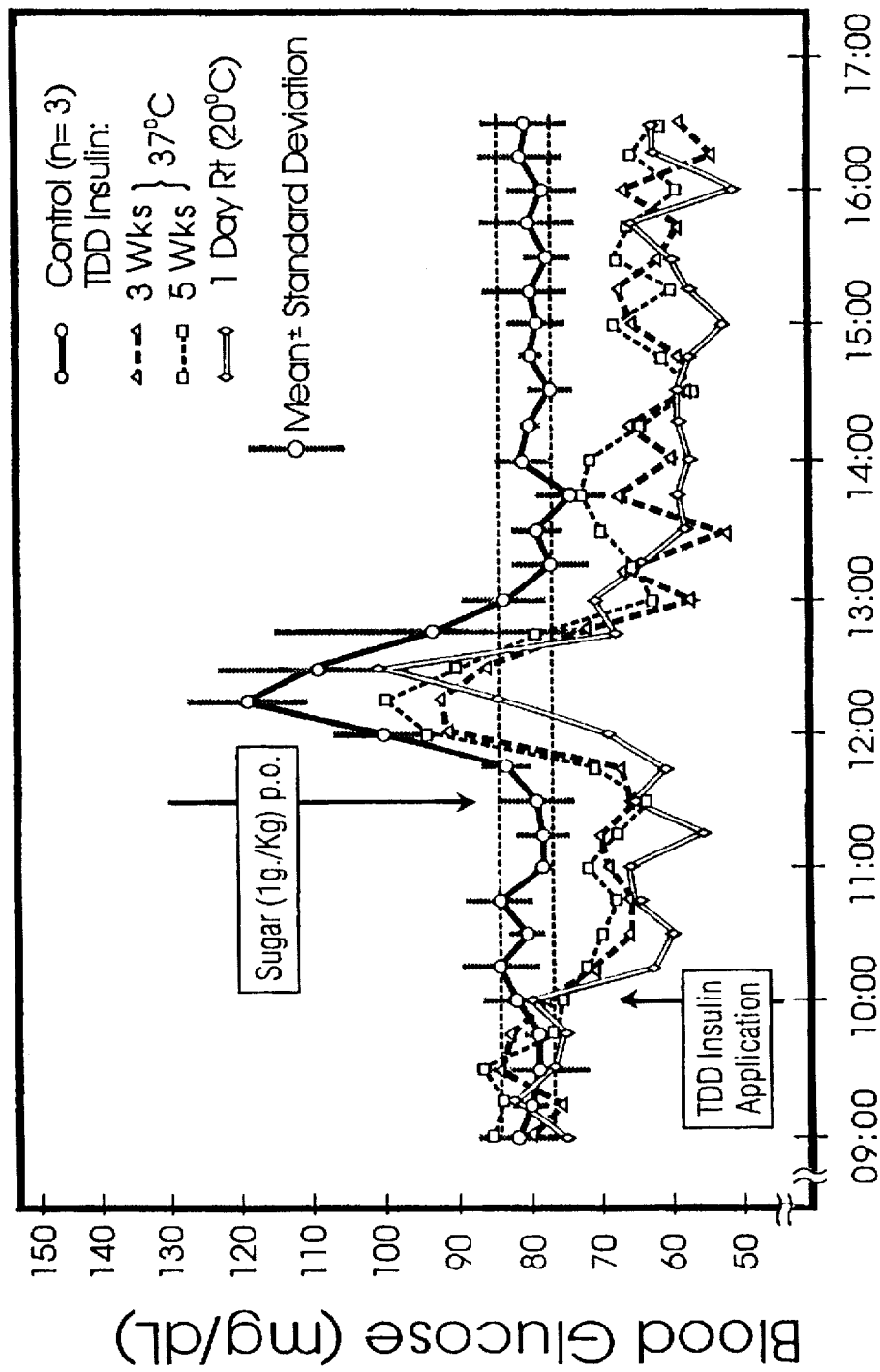
FIGS. 21 and 22 depict the effect of storage conditions on the activity of transdermal insulin formulations.

Transdermal insulin administration in a healthy subject—effect of storage conditions The present study was conducted to determine the stability of the transdermal dosage form (modified Formulation A), which contained the pretreated Actrapid (R) HM insulin solution (100 iu/ml), to which 20 mg of m-cresol were added after pretreatment, and just prior to the preparation of the formulation. Two similar dosage forms were prepared on the same day, one was placed in a closed Petri dish and stored at 2°–8° C. for five weeks, while the other was placed in a closed Petri dish and remained at room temperature (20° C.) until the following day, at which time it was tested on the subject. The modified glucose tolerance protocol was used to test the transdermal dosage forms. At the end of the protocol, the dosage form was removed, placed in a closed Petri dish and stored at 37° C. (incubator) for three weeks and then fetested. After the second testing, this dosage form was placed in a closed Petri dish and returned to the incubator (37° C.) for an additional two weeks (five weeks total) and then retested for the last time. Results of these tests are compared to the control experiment (Example 9), and presented in FIG. 21. Reduction in blood glucose as a result of the application of this dosage form on three occasions (6.5 hours each), separate by storage at 37° C. are not very different (FIG. 21).

Figure 22:
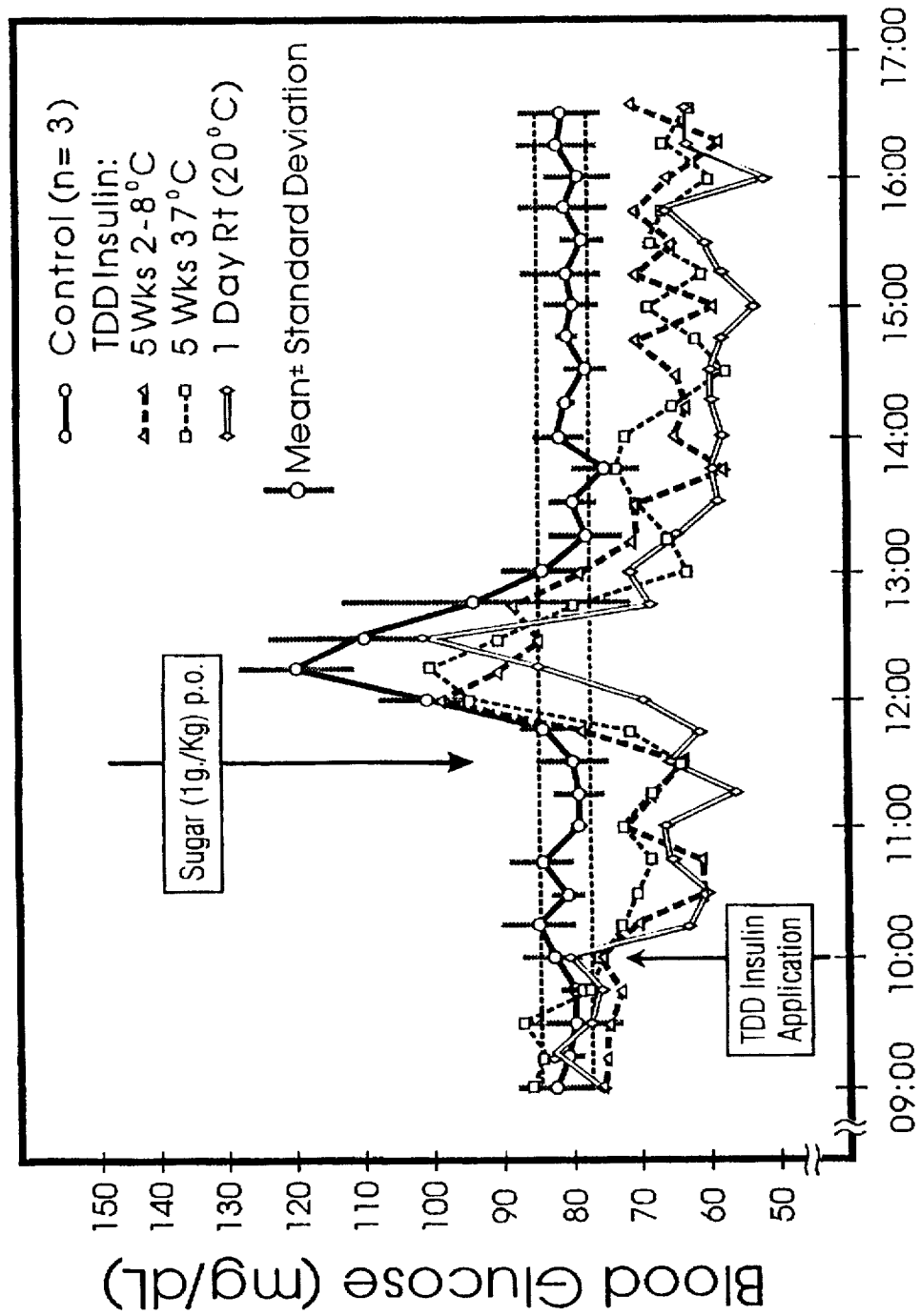

The second transdermal insulin dosage form was tested after storage at 2°–8° C. for five weeks, and the results compared with the previous tests after one day storage at 20° C. and after five weeks storage at 37° C. (FIG. 22). The results for the different from form were not very different from the first dosage form which was tested on three separate occasions and stored in the intervals at 37° C.

Results of this study show that the repeated use for nearly 20 hours of this transdermal insulin dosage form, plus storage for five weeks at 37° C. or 2°–8° C., had a minimal effect on this dosage form, in reducing the blood glucose level in a healthy subject.

EXAMPLE 19

Transdermal insulin administration in a healthy subject—hypoglycemia management

Hypoglycemia, which is a life-threatening situation if not treated immediately, is characterized by an abnormally low blood glucose level, and is experienced by virtually every insulin-dependent diabetic as a direct result of conventional insulin therapy.

The purpose of the present study was to effect a hypoglycemic event in which blood glucose concentration was less than 50 mg/dl, in a healthy subject, using the transdermal insulin dosage form and to simulate management of this event under the following alternative conditions:

(a) continuous insulin administration, with glucose administered additionally at hypoglycemia;

(b) cessation of insulin administration at hypoglycemia;

(c) cessation of insulin administration plus glucose administration, at hypoglycemia.

(a) CONTINUOUS INSULIN ADMINISTRATION, WITH GLUCOSE ADMINISTERED ADDITIONALLY AT HYPOGLYCEMIA

Figure 23:
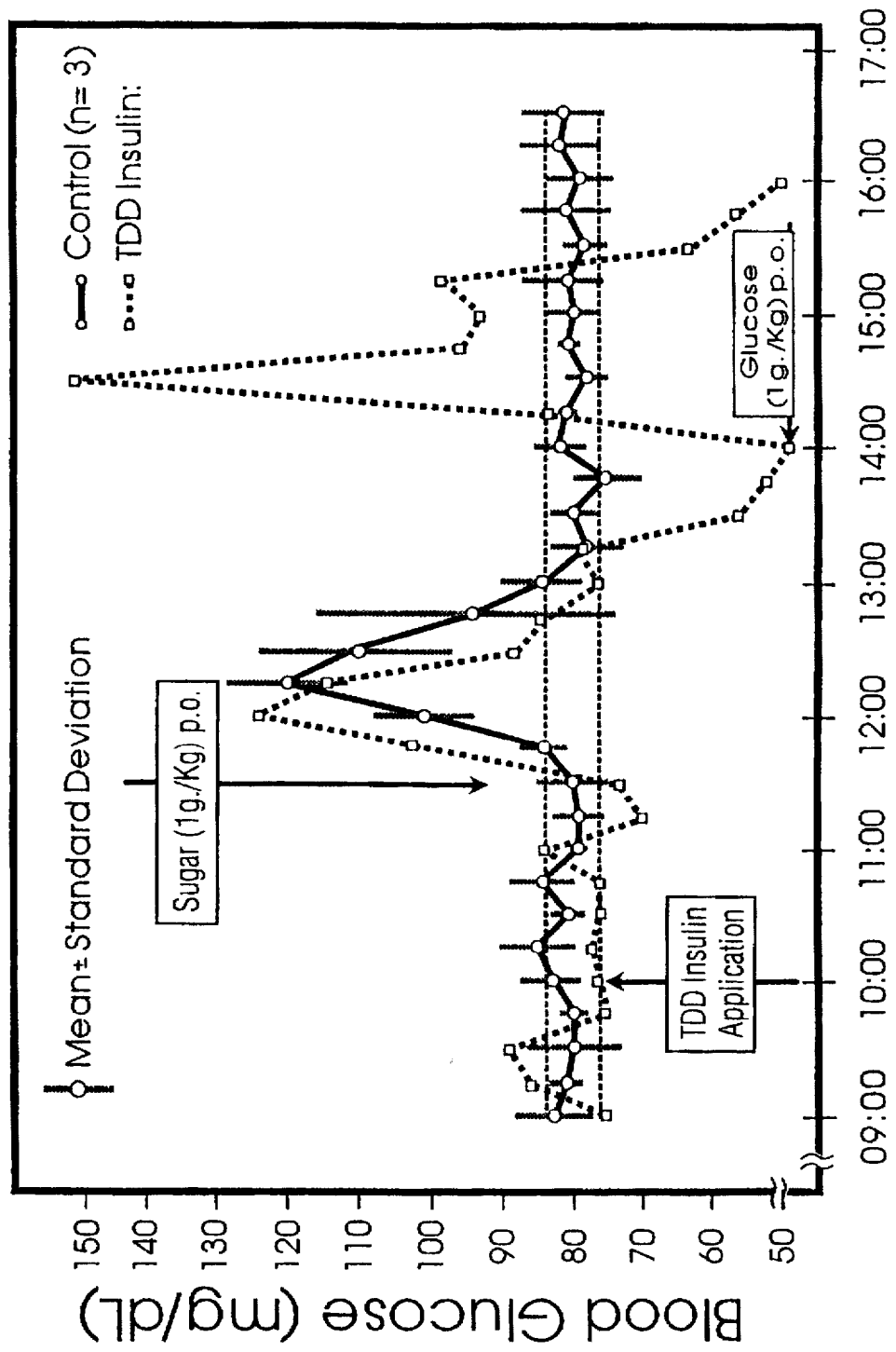
FIG. 23 depicts the effect of administration of a transdermal insulin formulation and hypoglycemia management.

Modified Formulation A was further modified in that 15% less lecithin was used. Pretreated Actrapid (R) HM insulin solution (500 iu/ml) was incorporated into this modified formulation. This further modified formulation resulted in delayed action, but caused blood glucose concentration to decrease to 45 mg/dl, following a sugar challenge (FIG. 23). At this point the subject ingested glucose (1 g/kg body weight) in solution, which resulted in a rapid rise of blood glucose concentration to 150 mg/dl, which rapidly fell back to 50 mg/dl within two hours, at which time the dosage form was removed and the experiment was terminated.

(b) CESSATION OF INSULIN ADMINISTRATION AT HYPOGLYCEMIA

In Example 15, transdermal administration of TDD insulin forte is described up to the point where blood glucose concentration fell to less than 50 mg/dl, when the dosage form was removed. Blood glucose was thereafter determined every 15 minutes until the end of the protocol. Results are presented in FIG. 24. Blood glucose concentration rose after removal of the dosage form, until control levels were reached, reflecting the regulatory mechanism of glucose mobilization in a healthy person, and showing that (in contrast with conventional parenteral administration, for example) administration of insulin could be effectively terminated by removal of the dosage form. ps (c) CESSATION OF INSULIN ADMINISTRATION PLUS GLUCOSE ADMINISTRATION, AT HYPOGLYCEMIA In Example 15, transdermal administration of TDD insulin forte (+) is described up to the point where blood glucose concentration fell to less than 45 mg/dl, when the dosage form was removed. Immediately thereafter, the subject drank the same amount of sugar solution as in the first part of the experiment and blood glucose was continued to be determined every 15 minutes until the end of the protocol. Results are presented in FIG. 25. Blood glucose concentration rose rapidly, reached control levels within 15 minutes, and had peaked at 120 mg/dl 45 minutes after ingestion, after which it fell and stabilized during the last hour of the protocol at approximately 70 mg/dl.

Figure 24:
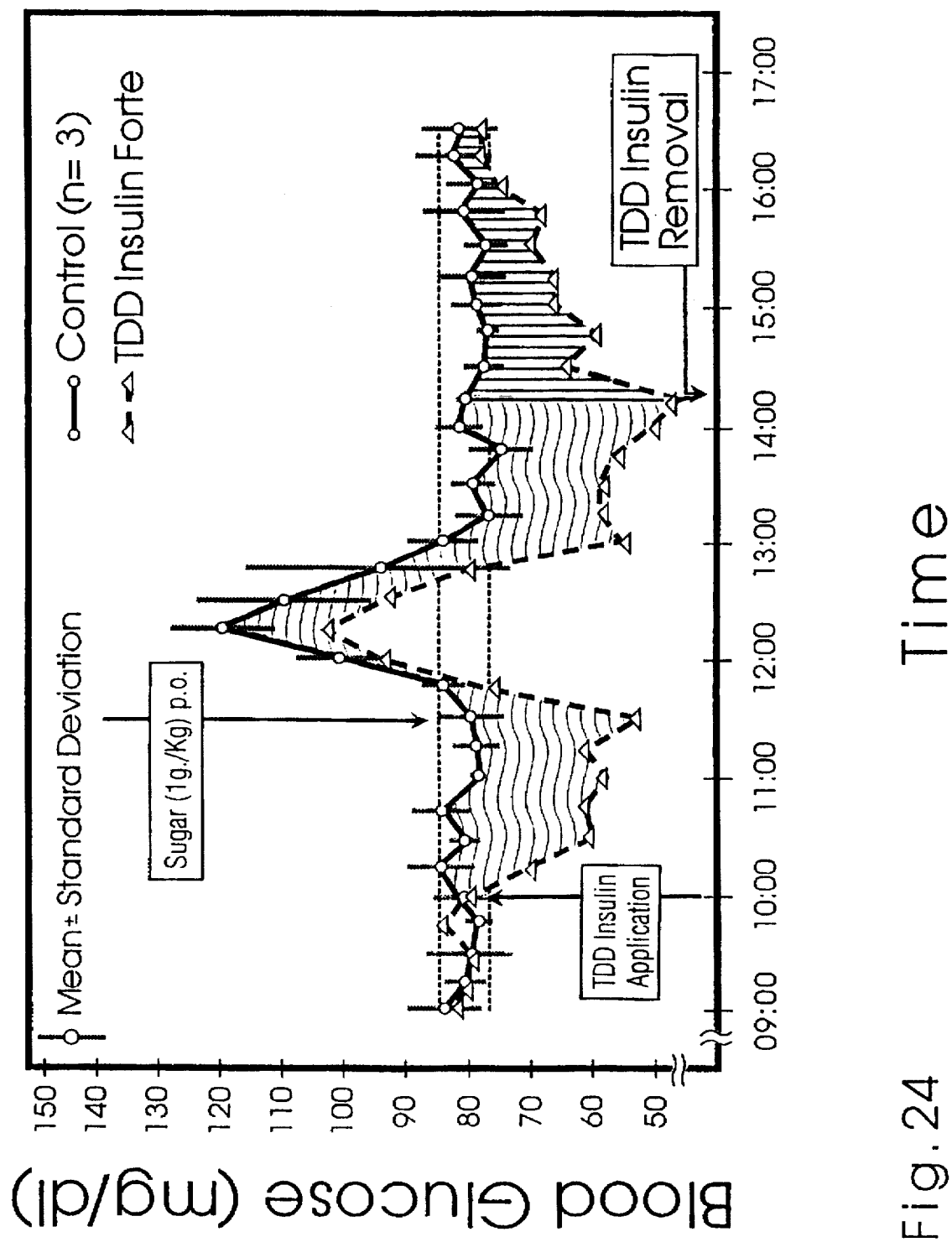
Figure 25:
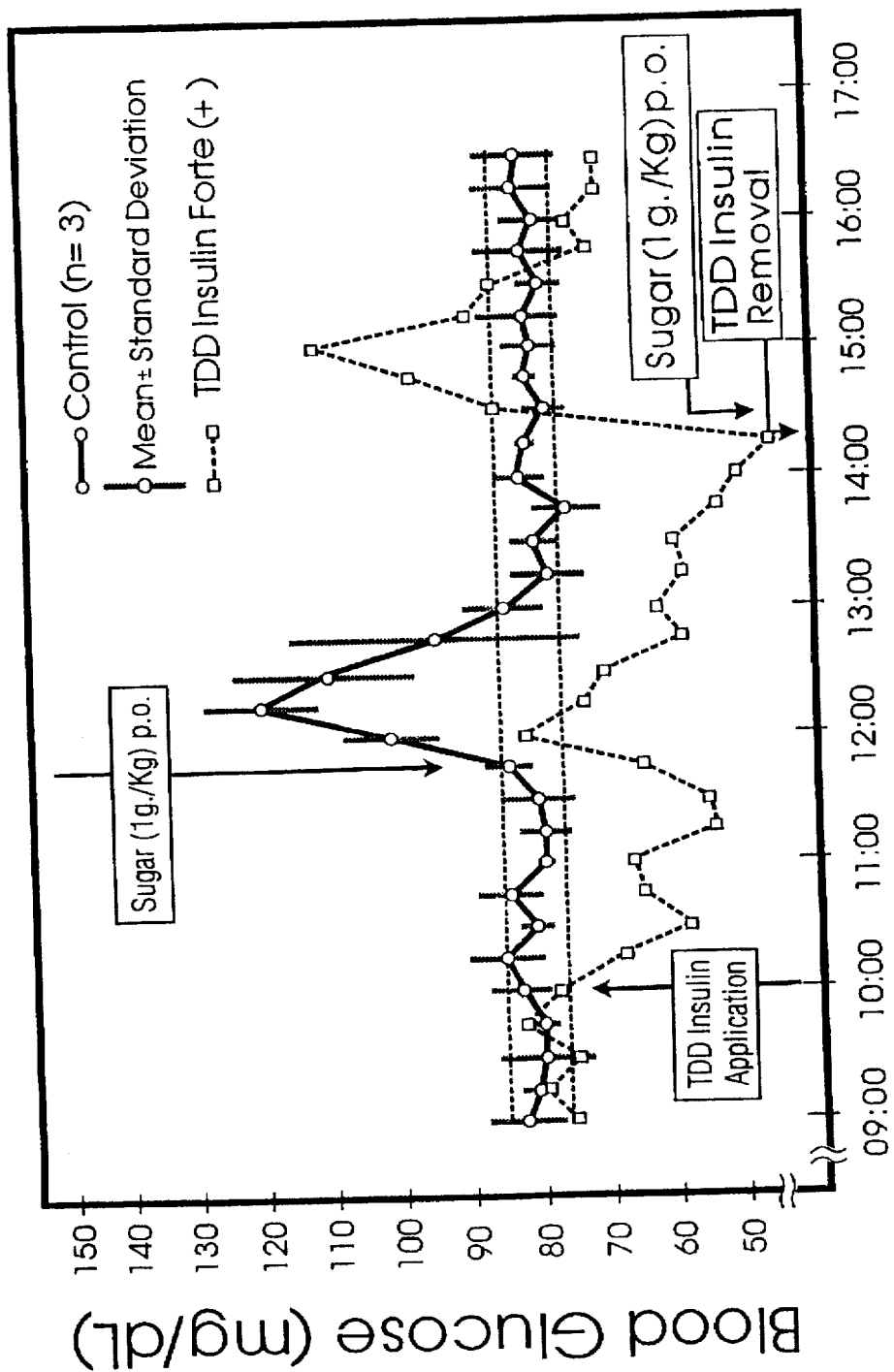

Results of this study show that insulin-induced hypoglycemia can be better and more safely controlled by removal of the transdermal dosage form (FIG. 24), compared with conventional subcutaneous injection, where excess insulin cannot be removed, but can only be neutralized by administration of glucose. This situation is simulated in FIG. 23, where it is seen that administration of glucose in presence of maintained insulin rapidly produces a further hypoglycemic event, whereas removing the transdermal dosage form according to the present invention terminates insulin administration, thus preventing a further decrease in blood glucose. Moreover, a comparison of FIG. 25 with FIG. 24, shows that when glucose is added immediately after removal of the transdermal dosage form, the hypoglycemic effect is arrested and an acceptable blood level of glucose is attained (i.e. avoiding hyperglycemia).

While the present invention is not to be limited by any theory, it is possible that the effect of pretreatment of insulin in accordance with the present invention may be due to dissociation of hexameric units into dimers and/or monomers, and possibly further dissociation of dimers into monomers, and/or dissociation of insulin units from the metal (commonly zinc, or possibly, e.g., magnesium) with which it is normally associated in commercial insulin preparations. The possibility is also presently contemplated that the emulsifier and/or the oil phase in particular embodiments of the present formulations are effective in preventing reassociation to hexamers and/or reformation of the insulin-metal bonds. It is further to be understood that the foregoing discussion includes the concept of weakening the association of insulin into hexamers, and/or weakening the insulin/metal bonds, in the formulations according to the invention. A person of the art will accordingly understand that insulin which is modified in that the hexamers are stably dissociated into dimers and/or monomers, and/or in which the insulin-metal bonds are split or weakened, are chemically equivalent to insulin in the present formulations, according to this concept of the invention, and thus that pharmaceutical formulations, dosage forms and therapeutic methods employing such modified insulin will be obvious equivalents of the present invention.

While presently preferred modes of operating the invention have been particularly described herein, it will be appreciated by those skilled in the art that many modifications and variations are possible. Merely by way of example, the insulin may take any of the forms mentioned in the preceding paragraph, or may be replaced by substituted insulins or insulin analogues, or by short-acting insulin preparations, all of which have been described in the literature available to a person of the art. It will also be apparent to a skilled person that, while the invention has been described herein with particular reference to insulin, which the inventors have found, contrary to previous indications in the literature, can be effectively administered transdermally, the formulations of the invention are also applicable to the administration of bioactive proteins other than insulin. Moreover, the skilled person will appreciate that the aspect of the invention which relates to use of both an aqueous phase and an oil phase, together with an emulsifier, will be capable of application to the administration of other therapeutic agents soluble in either the aqueous or the oil phase (or in both, or there may be used separate oil- and water-soluble therapeutic agents), e.g. transdermal administration of such therapeutic agents which are of similar molecular weight to, or of lower molecular weight than insulin, such as antibiotics, may be effected in this manner. The invention is thus not to be construed as limited by the modes of operation particularly described, but may be practised according to its concept, spirit or scope, as may be more readily understood by consideration of the appended claims.

We claim:

1. A pharmaceutical formulation which is adapted particularly for transdermal administration, and which comprises an aqueous emulsion or dispersion including, in addition to the aqueous phase, at least the following ingredients (a), (b) and (c):
   (a) an active ingredient which comprises insulin;
   (b) at least one pharmaceutically acceptable emulsifier;
   (c) an oil phase comprising at least one ester of an aliphatic hydroxy compound containing 1–12 carbon atoms and 1–4 alcoholic hydroxy groups with an aliphatic carboxylic acid containing 8–24 carbon atoms and 1–3 carboxylic acid groups;
   provided that the therapeutic activity of said active ingredient is such that the presence or the therapeutic effect of said active ingredient is detectable in the bloodstream in less than two hours after commencing transdermal administration of said formulation,
   and further provided that said insulin has been subjected to a pretreatment under predetermined conditions above refrigeration temperature, prior to incorporation in said formulation, said pretreatment being sufficient to produce said therapeutic activity.

2. A pharmaceutical formulation according to claim 1, wherein the activity of the insulin therein is such that in a bioassay based on subcutaneous injection of no more than 0.2 iu insulin/kg in healthy rabbits, including a control bioassay, the formulation is capable of exhibiting a peak of reduction of the blood glucose concentration, compared with the control, within no more than one hour from the time of injection.

3. A pharmaceutical formulation according to claim 2, wherein said peak of reduction is at least 50% below the control value of blood glucose concentration.

4. A pharmaceutical formulation according to claim 1, wherein said at least one ester is selected from the group consisting of monoglycerides, diglycerides and triglycerides of monocarboxylic acids selected from the group consisting of saturated monocarboxylic acids and monocarboxylic acids containing ethylenic unsaturation.

5. A pharmaceutical formulation according to claim 1, wherein said pharmaceutically acceptable emulsifier contains at least one esterified carboxylic group in its structure.

6. A pharmaceutical formulation according to claim 5, wherein said pharmaceutically acceptable emulsifier is selected from the group consisting of lecithin and polyoxyethylene sorbitan monocarboxylate esters.

7. A pharmaceutical formulation which is adapted particularly for transdermal administration, and which comprises at least one carrier, diluent or adjuvant, together with insulin as active ingredient, provided that said insulin has been subjected to a pretreatment under predetermined conditions above refrigeration temperature sufficient to cause its therapeutic activity to be such that the presence or the therapeutic effect of said active ingredient is detectable in the bloodstream in less than two hours after commencing transdermal administration of said formulation;

and provided further that said formulation does not contain didecanoyl-α-phosphatidyl choline.

8. A pharmaceutical formulation according to claim 7, wherein the activity of the insulin therein is such that in a bioassay based on subcutaneous injection of no more than 0.2 iu insulin/kg in healthy rabbits, including a control bioassay, the formulation is capable of exhibiting a peak of reduction of the blood glucose concentration, compared with the control, within no more than one hour from the time of injection.

9. A pharmaceutical formulation according to claim 8, wherein said peak of reduction is at least 50% below the control value of blood glucose concentration.

10. A matrix for transdermal administration of at least one active ingredient which comprises insulin, which comprises a porous, absorbent, perforate and flexible monolaminar or polylaminar solid support, having absorbed thereon a pharmaceutical formulation according to claim 1.

11. A matrix for transdermal administration of a pharmaceutical formulation containing insulin, which comprises a porous, absorbent, perforate and flexible monolaminar or polylaminar solid support, having absorbed thereon a pharmaceutical formulation according to claim 7.

12. A method for controlling glucose concentration in the blood of a diabetic patient, which comprises transdermally administering to said patient a pharmaceutical formulation according to claim 1.

13. A method according to claim 12, wherein said transdermal administration is effected by applying to the skin of the patient a matrix which comprises a porous, absorbent, perforate and flexible monolaminar or polylaminar solid support, having absorbed thereon said pharmaceutical formulation.

14. A method for controlling glucose concentration in the blood of as diabetic patient, which comprises administering to the patient a pharmaceutical formulation according to claim 7.

15. A method according to claim 14, wherein said pharmaceutical formulation is administered to the patient transdermally.

16. A method according to claim 15, wherein said transdermal administration is effected by applying to the skin of the patient a matrix which comprises a porous, absorbent, perforate and flexible monolaminar or polylaminar solid support, having absorbed thereon said pharmaceutical formulation.

17. A pharmaceutical formulation which is adapted particularly for transdermal administration, and which comprises an aqueous emulsion or dispersion including, in addition to the aqueous phase, at least the following ingredients (a) and (b):

(a) an active ingredient comprising insulin; and
(b) at least one pharmaceutically acceptable emulsifier;

provided that the formulation excludes didecanoyl-α-phosphatidyl choline, that the therapeutic activity of said active ingredient in said formulation is such that the presence or the therapeutic effect of said active ingredient is detectable in the bloodstream in less than two hours after commencing transdermal administration of said formulation, and provided that said insulin has been subjected to a pretreatment under predetermined conditions above refrigeration temperature, prior to incorporation of said insulin in said formulation, said pretreatment being sufficient to produce said therapeutic activity.

18. A pharmaceutical formulation according to claim 17, wherein the activity of said insulin is such that in a bioassay based on subcutaneous injection of no more than 0.2 iu insulin/kg in healthy rabbits, including a control bioassay, said formulation is capable of exhibiting a peak of reduction of the blood glucose concentration, compared with the control, within no more than one hour from the time of injection of said formulation.

19. A pharmaceutical formulation according to claim 18, wherein said peak of reduction is at least 50% below the control value of blood glucose concentration.

20. A pharmaceutical formulation according to claim 17, wherein said at least one ester is selected from the group consisting of monoglycerides, diglycerides and triglycerides of monocarboxylic acids selected from the group consisting of saturated monocarboxylic acids and monocarboxylic acids containing ethylenic unsaturation.

21. A pharmaceutical formulation according to claim 17, wherein said pharmaceutically acceptable emulsifier contains at least one esterified carboxylic group in its structure.

22. A pharmaceutical formulation according to claim 21, wherein said pharmaceutically acceptable emulsifier is selected from the group consisting of lecithin and polyoxyethylene sorbitan monocarboxylate esters.

23. A matrix for transdermal administration of insulin, which comprises a porous, absorbent, perforate and flexible monolaminar or polylaminar solid support, having absorbed thereon a pharmaceutical formulation according to claim 17.

24. A method for controlling glucose concentration in the blood of as diabetic patient, which comprises administering to the patient a pharmaceutical formulation according to claim 17.

25. A method according to claim 24, wherein said pharmaceutical formulation is administered to said patient transdermally.

26. A method according to claim 25, wherein said transdermal administration is effected by applying to the skin of said patient a matrix which comprises a porous, absorbent, perforate and flexible monolaminar or polylaminar solid support, having absorbed thereon said pharmaceutical formulation.

27. A pharmaceutical formulation which is adapted particularly for transdermal administration, and which comprises an aqueous emulsion or dispersion including, in addition to the aqueous phase, an active ingredient which comprises insulin which is stably dissociated into dimers and/or monomers and/or in which insulin-metal bonds are split or weakened, and substituted insulin or short-acting insulin preparations, wherein the therapeutic activity of said active ingredient is such that the presence or the therapeutic effect of said active ingredient is detectable in the bloodstream in less than two hours after commencing transdermal administration of said formulation.

* * * * *